(12) United States Patent
Boonzaier et al.

(10) Patent No.: US 12,409,003 B2
(45) Date of Patent: Sep. 9, 2025

(54) INSTRUMENT CASSETTE ASSEMBLIES FOR ROBOTIC SURGICAL INSTRUMENTS

(71) Applicant: Titan Medical, Inc., Toronto (CA)

(72) Inventors: James A. Boonzaier, Cape Town (ZA); Jack A. Hornsby, Tempsford (GB); Akshaya Ahuja, St. Neots (GB); Aki Hannu Einari Laakso, Raleigh, NC (US); Hans C. Pflaumer, Apex, NC (US); Rupert A. Barton, Cambridge (GB); Adam R. Turner, Cambridge (GB); Paul Smitheman, Cambridge (GB); Matthew J. Brady, Cambridge (GB)

(73) Assignee: Covidien LP, Mansfield, MA (US)

( * ) Notice: Subject to any disclaimer, the term of this patent is extended or adjusted under 35 U.S.C. 154(b) by 605 days.

(21) Appl. No.: 17/686,749

(22) Filed: Mar. 4, 2022

(65) Prior Publication Data

US 2022/0361971 A1 Nov. 17, 2022

Related U.S. Application Data

(60) Provisional application No. 63/188,554, filed on May 14, 2021.

(51) Int. Cl.
| | |
|---|---|
| A61B 34/37 | (2016.01) |
| A61B 34/00 | (2016.01) |
| A61B 34/30 | (2016.01) |
| A61B 34/35 | (2016.01) |
| A61B 90/50 | (2016.01) |

(52) U.S. Cl.
CPC .............. *A61B 34/37* (2016.02); *A61B 34/35* (2016.02); *A61B 34/71* (2016.02); *A61B 90/50* (2016.02); *A61B 2034/301* (2016.02); *A61B 2034/302* (2016.02)

(58) Field of Classification Search
None
See application file for complete search history.

(56) References Cited

U.S. PATENT DOCUMENTS

| | | | | |
|---|---|---|---|---|
| 5,582,617 | A | * 12/1996 | Klieman | ................ A61B 34/71 606/174 |
| 6,132,368 | A | 10/2000 | Cooper | |
| 6,206,903 | B1 | 3/2001 | Ramans | |

(Continued)

OTHER PUBLICATIONS

Extended European Search Report for application No. 22173358.7 dated Oct. 10, 2022.

*Primary Examiner* — Benjamin J Klein
*Assistant Examiner* — Willow Grace Welch
(74) *Attorney, Agent, or Firm* — Carter, DeLuca & Farrell LLP

(57) ABSTRACT

A surgical instrument of a robotic surgical system includes an elongated shaft assembly, and end effector, and an instrument cassette assembly. The elongated shaft assembly has a proximal end portion and a distal end portion. The end effector is supported the distal end portion of the elongated shaft assembly. The instrument cassette assembly is supported on the proximal end portion of the elongated shaft assembly. The instrument cassette assembly includes a cassette housing and an actuator system supported in the cassette housing. The actuator system is operably coupled to the end effector for operating the end effector.

20 Claims, 29 Drawing Sheets

(56) References Cited

U.S. PATENT DOCUMENTS

| | | |
|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |

(56) References Cited

U.S. PATENT DOCUMENTS

| | | |
|---|---|---|
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Arkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |

(56) References Cited

U.S. PATENT DOCUMENTS

| | | |
|---|---|---|
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2002/0188293 A1* | 12/2002 | Manzo .................. A61B 34/30 606/45 |
| 2008/0087871 A1 | 4/2008 | Schena |
| 2014/0005681 A1* | 1/2014 | Gee .................... A61F 9/00745 606/130 |
| 2014/0249545 A1* | 9/2014 | Hyodo .................. A61B 34/30 606/130 |
| 2014/0249557 A1* | 9/2014 | Koch, Jr. ......... A61B 17/32002 606/170 |
| 2014/0257333 A1 | 9/2014 | Blumenkranz |
| 2019/0150904 A1 | 5/2019 | Robert et al. |
| 2021/0137618 A1 | 5/2021 | Simi et al. |
| 2021/0290314 A1 | 9/2021 | Sachs et al. |

* cited by examiner

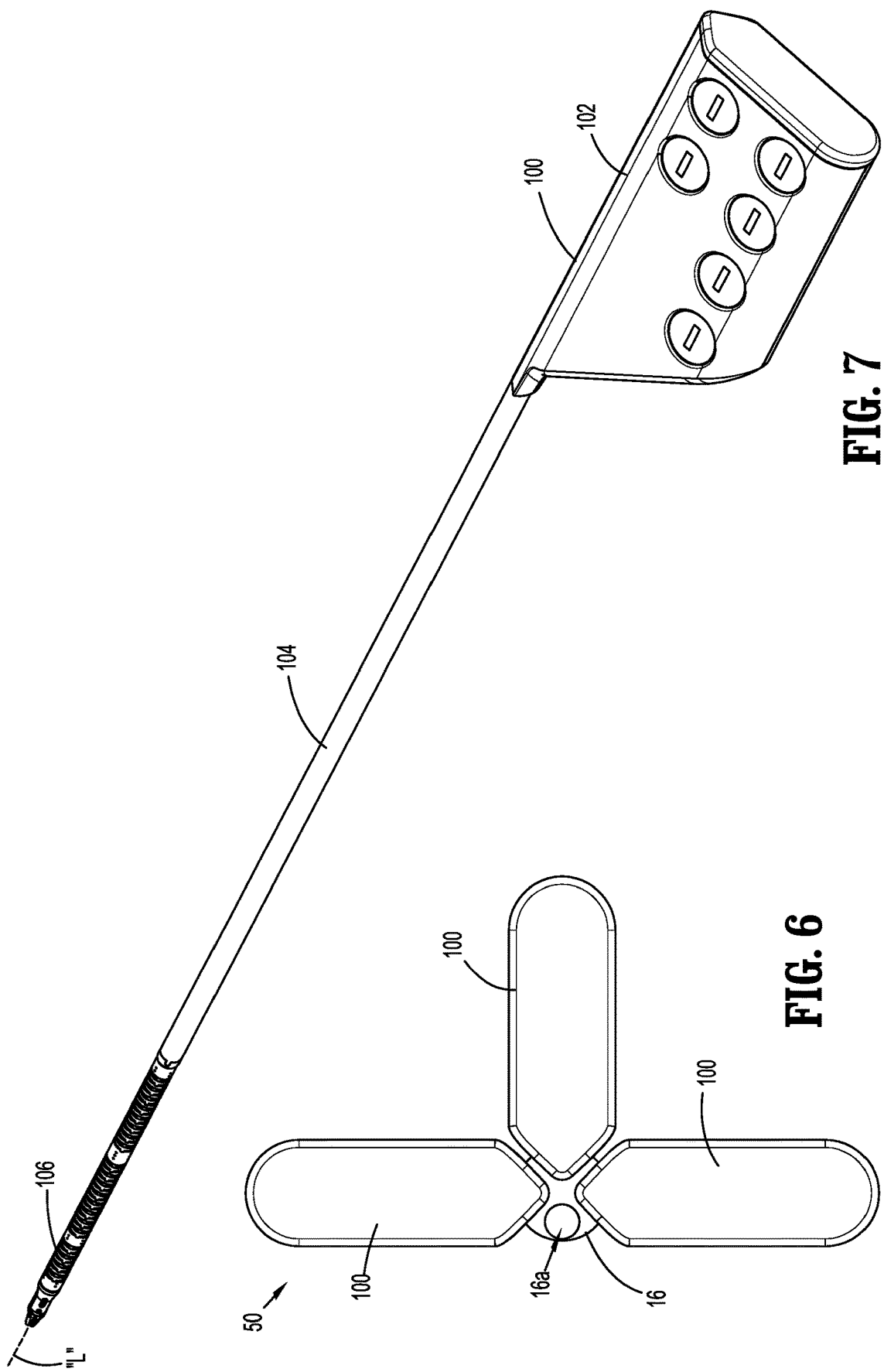

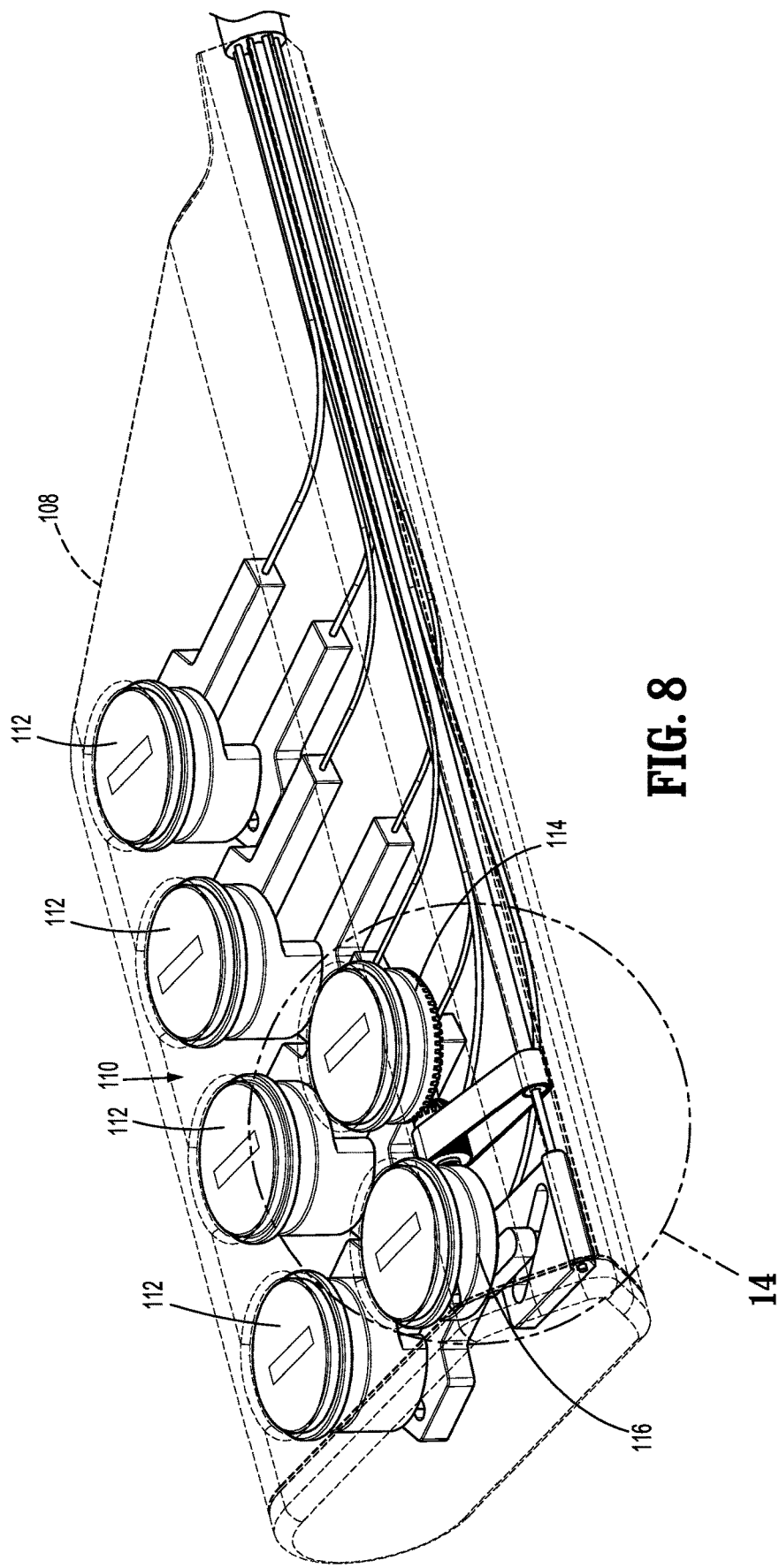

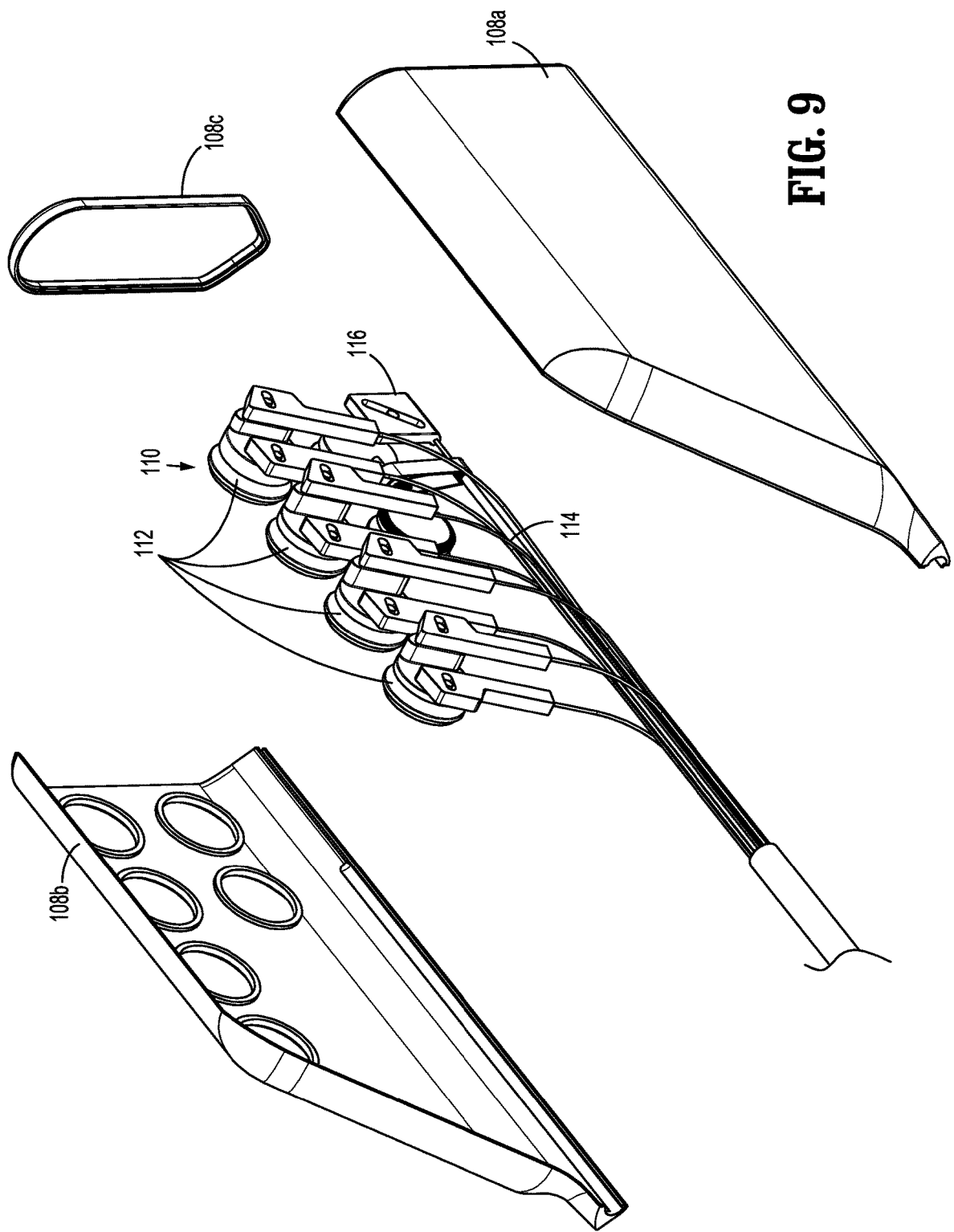

INSTRUMENT CASSETTE ASSEMBLIES FOR ROBOTIC SURGICAL INSTRUMENTS

CROSS REFERENCE TO RELATED APPLICATIONS

This application claims the benefit of U.S. Provisional Application Ser. No. 63/188,554, filed May 14, 2021, the entire contents of which are incorporated by reference herein.

TECHNICAL FIELD

This disclosure relates to robotic systems and, more particularly, to instrument cassettes for robotic surgical instruments.

BACKGROUND

Surgical instruments used in laparoscopic and/or robotic surgery generally have a proximally located actuating mechanism that may be used to actuate a distal end effector for performing a surgical task within a body cavity of a patient. Such instruments may be used in applications where there is an area of limited access for an operator. The distal end of the instrument may be inserted into the area of limited access and the operator may remotely and/or robotically manipulate the instrument via the actuator mechanism.

SUMMARY

In accordance with an aspect of this disclosure, a robotic surgical system includes a drive unit and a surgical instrument removably connected to the drive unit. The surgical instrument includes an elongated shaft assembly, an end effector, and an instrument cassette assembly. The elongated shaft assembly has a proximal end portion and a distal end portion. The end effector is supported the distal end portion of the elongated shaft assembly. The instrument cassette assembly is supported on the proximal end portion of the elongated shaft assembly. The instrument cassette assembly includes a cassette housing, an actuator system supported in the cassette housing and operably coupled to the end effector for operating the end effector. The actuator system includes a cable actuator assembly, a shaft assembly defining a longitudinal axis, a rotation actuator assembly, and an axial actuator assembly. The cable actuator assembly includes a plurality of cables that extends from the cassette housing to the end effector for manipulating the end effector. The rotation actuator assembly is coupled to the shaft assembly and positioned to rotate the shaft assembly about the longitudinal axis for imparting rotational force to the end effector. The axial actuator assembly is coupled to the shaft assembly and positioned to axially translate the shaft assembly relative to the longitudinal axis for imparting axial force to the end effector.

In aspects, the cable actuator assembly may include a crank, a first slider, and a second slider, the first and second sliders coupled to the crank. The crank may be rotatable to linearly translate the first and second sliders relative to one another. The first slider may support a first cable of the plurality of cables and the second slider may support a second cable of the plurality of cables. The crank may be coupled to a driver that is engaged with the drive unit. The driver may be configured to impart rotational force on the crank.

In aspects, the rotation actuator assembly may include a drive wheel and a belt drive shaft supporting a belt. The belt may be coupled to the shaft assembly and the drive wheel may be coupled to the belt drive shaft. The drive wheel and the belt drive may be disposed transverse to one another. The drive wheel may be configured to rotate the belt drive shaft. Rotation of the belt drive shaft may rotate the belt to rotate the shaft assembly.

In aspects, the axial actuator assembly may include a drive disc, a drive arm coupled to the drive disc, and a drive plate coupled to the drive arm and to the shaft assembly. In aspects, the drive arm may include a first pin coupled to the drive disc and a second pin coupled to the drive plate. The drive plate may define a pin slot that receives the second pin. The second pin may be slidable along the pin slot to axially translate the drive plate and the shaft assembly as the drive disc rotates.

According to one aspect, this disclosure is directed to a surgical system including a cassette housing and an actuator system. The actuator system is supported in the cassette housing and includes a cable actuator, a shaft assembly, a rotation actuator assembly, and an axial actuator assembly. The cable actuator assembly includes a plurality of cables. The shaft assembly defines a longitudinal axis. The rotation actuator assembly is coupled to the shaft assembly and positioned to rotate at least a portion of the shaft assembly about the longitudinal axis. The axial actuator assembly is coupled to the shaft assembly and positioned to axially translate at least a portion of the shaft assembly relative to the longitudinal axis.

According to another aspect, this disclosure is directed to a surgical instrument for a robotic surgical system. The surgical instrument includes an elongated shaft assembly, an end effector, and an instrument cassette assembly. The elongated shaft assembly has a proximal end portion and a distal end portion. The end effector is supported at the distal end portion of the elongated shaft assembly. The instrument cassette assembly is supported on the proximal end portion of the elongated shaft assembly. The instrument cassette assembly includes a cassette housing and an actuator system. The actuator system is supported in the cassette housing and operably coupled to the end effector for operating the end effector. The actuator system includes a cable actuator assembly, a shaft assembly, a rotation actuator assembly, and an axial actuator assembly. The cable actuator assembly includes a plurality of cables that extends from the cassette housing to the end effector for manipulating the end effector. The shaft assembly defines a longitudinal axis. The rotation actuator assembly is coupled to the shaft assembly and positioned to rotate the shaft assembly about the longitudinal axis for imparting rotational force to the end effector. The axial actuator assembly is coupled to the shaft assembly and positioned to axially translate the shaft assembly relative to the longitudinal axis for imparting axial force to the end effector.

According to still another aspect, this disclosure is directed to a robotic surgical system. The robotic surgical system includes a drive unit and a surgical instrument removably connected to the drive unit. The surgical instrument includes an elongated shaft assembly, an end effector, and an instrument cassette assembly. The elongated shaft assembly has a proximal end portion and a distal end portion. The end effector is supported on the distal end portion of the elongated shaft assembly. The instrument cassette assembly is supported on the proximal end portion of the elongated shaft assembly. The instrument cassette assembly includes a cassette housing and an actuator system. The actuator system is supported in the cassette housing and is operably coupled to the end effector for operating the end effector. The actuator system includes a cable actuator assembly including a spindle, an upper crank, and a lower crank. The upper crank is coupled to a first cable and the lower crank is coupled to a second cable. The upper and lower cranks are movable along the spindle to move the first and second cables for manipulating the end effector.

In aspects, the first and second cables may be movable relative to one another.

In aspects, the drive unit may rotate the spindle about a spindle axis. Rotation of the spindle may cause the upper and lower cranks to translate along the spindle axis. The upper and lower cranks may translate in opposite directions along the spindle axis.

In aspects, the second cable may extend through the lower crank. The lower crank may include a spine through which the second cable slides as the upper crank moves relative to the lower crank.

In aspects, the upper crank may define a first spiral passage through an outer surface thereof. The lower crank may define a second spiral passage through an outer surface thereof. The second spiral passage may turn in an opposite direction than the first spiral passage. The spindle may include a first pin that slides through the first spiral passage and a second pin that slides through the second spiral passage.

According to another aspect, this disclosure is directed to a surgical system. The surgical system includes a cassette housing and an actuator system. The actuator system is supported in the cassette housing. The actuator system includes a cable actuator assembly including a spindle, an upper crank, and a lower crank. The upper crank is coupled to a first cable. The lower crank is coupled to a second cable. The upper and lower cranks are movable along the spindle to move the first and second cables.

In aspects, the spindle may rotate about a spindle axis to cause the upper and lower cranks to translate along the spindle axis.

According to still another aspect, this disclosure is directed to a surgical instrument for a robotic surgical system. The surgical instrument includes an elongated shaft assembly, an end effector, an instrument cassette assembly. The elongated shaft assembly has a proximal end portion and a distal end portion. The end effector is supported the distal end portion of the elongated shaft assembly. The instrument cassette assembly is supported on the proximal end portion of the elongated shaft assembly. The instrument cassette assembly includes a cassette housing and a cable actuator assembly. The cable actuator assembly is supported in the cassette housing and includes a spindle, an upper crank, and a lower crank. The upper crank is coupled to a first cable. The lower crank is coupled to a second cable. The upper and lower cranks are translatable along the spindle to move the first and second cables for manipulating the end effector as the spindle rotates relative to the upper and lower cranks.

According to yet another aspect, this disclosure is directed to a robotic surgical system. The robotic surgical system includes a drive unit and a surgical instrument removably connected to the drive unit. The surgical instrument includes an elongated shaft assembly, an end effector, and an instrument cassette assembly. The elongated shaft assembly has a proximal end portion and a distal end portion. The end effector is supported on the distal end portion of the elongated shaft assembly. The instrument cassette assembly is supported on the proximal end portion of the elongated shaft assembly. The instrument cassette assembly includes a cassette housing and an actuator system. The actuator system is supported in the cassette housing and operably coupled to the end effector for operating the end effector. The actuator system includes a cable actuator assembly and a drive actuator assembly. The cable actuator assembly includes a crank that supports an upper slider and a lower slider. The upper and lower sliders are coupled to cables that extend to the end effector. The drive actuator assembly includes a rotation actuator assembly and an axial actuator assembly. The rotation actuator assembly has at least one spool that rotates an inner shaft assembly coupled to the end effector to impart rotational force to the end effector. The axial actuator assembly includes a pivotable clevis that moves an axial drive cable relative to the inner shaft assembly to impart axial force to the end effector.

In aspects, the crank may be coupled to the upper and lower sliders by first and second pins. The first pin may be slidably positioned within an elongated pin slot defined in the upper slider and the second pin may be slidably positioned within an elongated pin slot defined in the lower slider. The upper slider and lower slider may be positioned to translate in opposite directions as the crank rotates.

In aspect, the at least one spool of the rotation actuator assembly may include an input spool and an output spool that are coupled together by a rotation cable. The input spool may be nonrotatably coupled to a driver, the input spool configured to rotate when the driver rotates. Rotation of the input spool moves the rotation cable about the output spool to rotate the inner shaft assembly.

In aspects, the axial actuator assembly may include a threaded nut that is pinned to the pivotable clevis to enable the pivotable clevis to pivot relative to the threaded nut. The threaded nut may be threadedly coupled to a threaded driver. The threaded driver may be rotatable to cause the threaded nut to translate along the threaded driver. Translation of the threaded nut along the threaded driver may cause the pivotable clevis to pivot about a mounting protrusion such that the axial drive cable moves between extended and retracted positions relative to the inner shaft assembly.

According to one aspect, this disclosure is directed to a surgical system. The surgical system includes a cassette housing and an actuator system supported in the cassette housing. The actuator system includes a cable actuator assembly and a drive actuator assembly. The cable actuator assembly includes a crank that supports an upper slider and a lower slider. The upper and lower sliders are coupled to cables. The drive actuator assembly includes a rotation actuator assembly and an axial actuator assembly. The rotation actuator assembly has at least one spool that rotates an inner shaft assembly. The axial actuator assembly includes a pivotable clevis that moves an axial drive cable relative to the inner shaft assembly.

According to yet another aspect, this disclosure is directed to a surgical instrument for a robotic surgical system. The surgical instrument includes an elongated shaft assembly, an end effector, a cassette housing, and a drive actuator assembly. The elongated shaft assembly has a proximal end portion and a distal end portion. The elongated shaft assembly includes an inner shaft assembly. The end effector is supported the distal end portion of the elongated shaft assembly. The cassette housing is supported on the proximal end portion of the elongated shaft assembly. The drive actuator assembly is supported in the cassette housing and is operably coupled to the end effector for operating the end effector. The drive actuator assembly includes a rotation actuator assembly and an axial actuator assembly. The rotation actuator assembly has a spool that rotates the inner shaft assembly to impart rotational force to the end effector. The axial actuator assembly includes a pivotable clevis that moves an axial drive cable relative to the inner shaft assembly to impart axial force to the end effector.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate aspects of this disclosure and, together with a general description of this disclosure given above, and the detailed description given below, explain the principles of this disclosure, wherein:

FIG. 6 is an enlarged top view of FIG. 5;

FIG. 7 is a perspective view of one surgical instrument of the surgical instruments shown in FIG. 5;

FIG. 8 is an enlarged, perspective view of an instrument cassette assembly of the surgical instrument of FIG. 7 with portions thereof shown in phantom for clarity;

FIG. 9 is a perspective view, with parts separated, of the instrument cassette assembly of FIG. 8;

DETAILED DESCRIPTION

Figure 1:
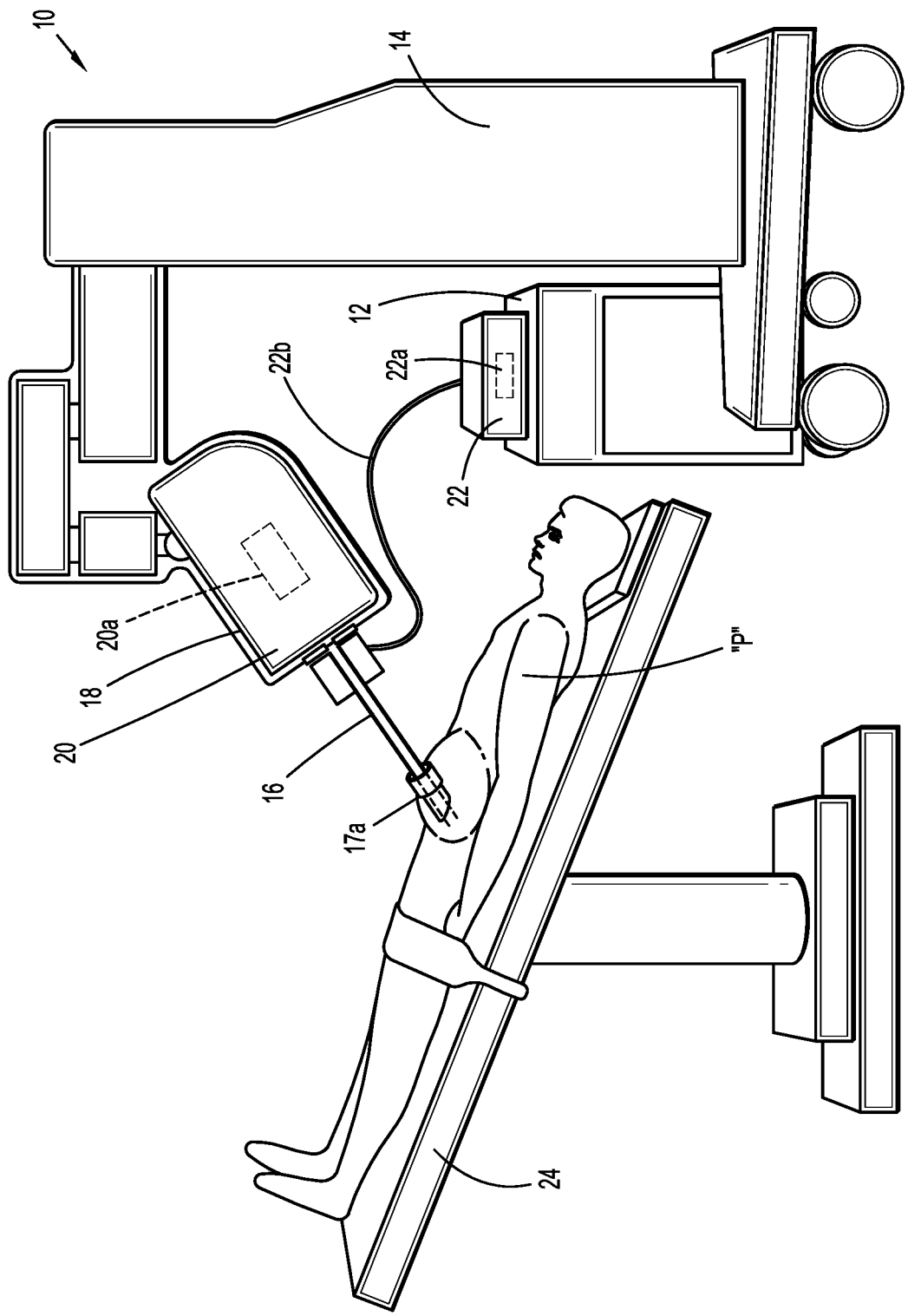
FIG. 1 is a perspective view of a robotic surgical system being used for a surgical procedure on a patient in accordance with the principles of this disclosure.
Figure 2:
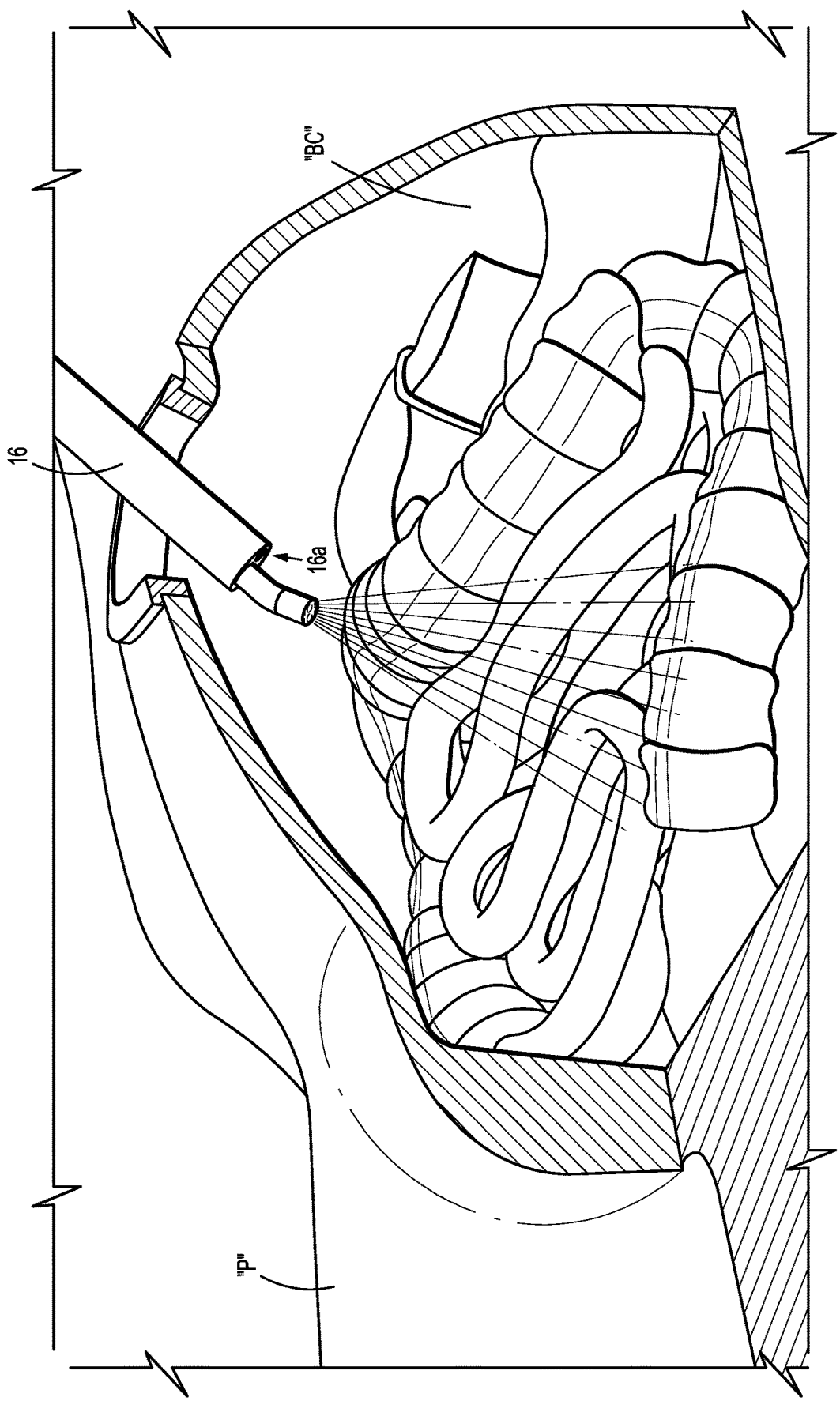
FIGS. 2-4 are progressive views illustrating surgical instruments of the robotic surgical system of FIG. 1 being manipulated within a body cavity of the patient.
Figure 3:
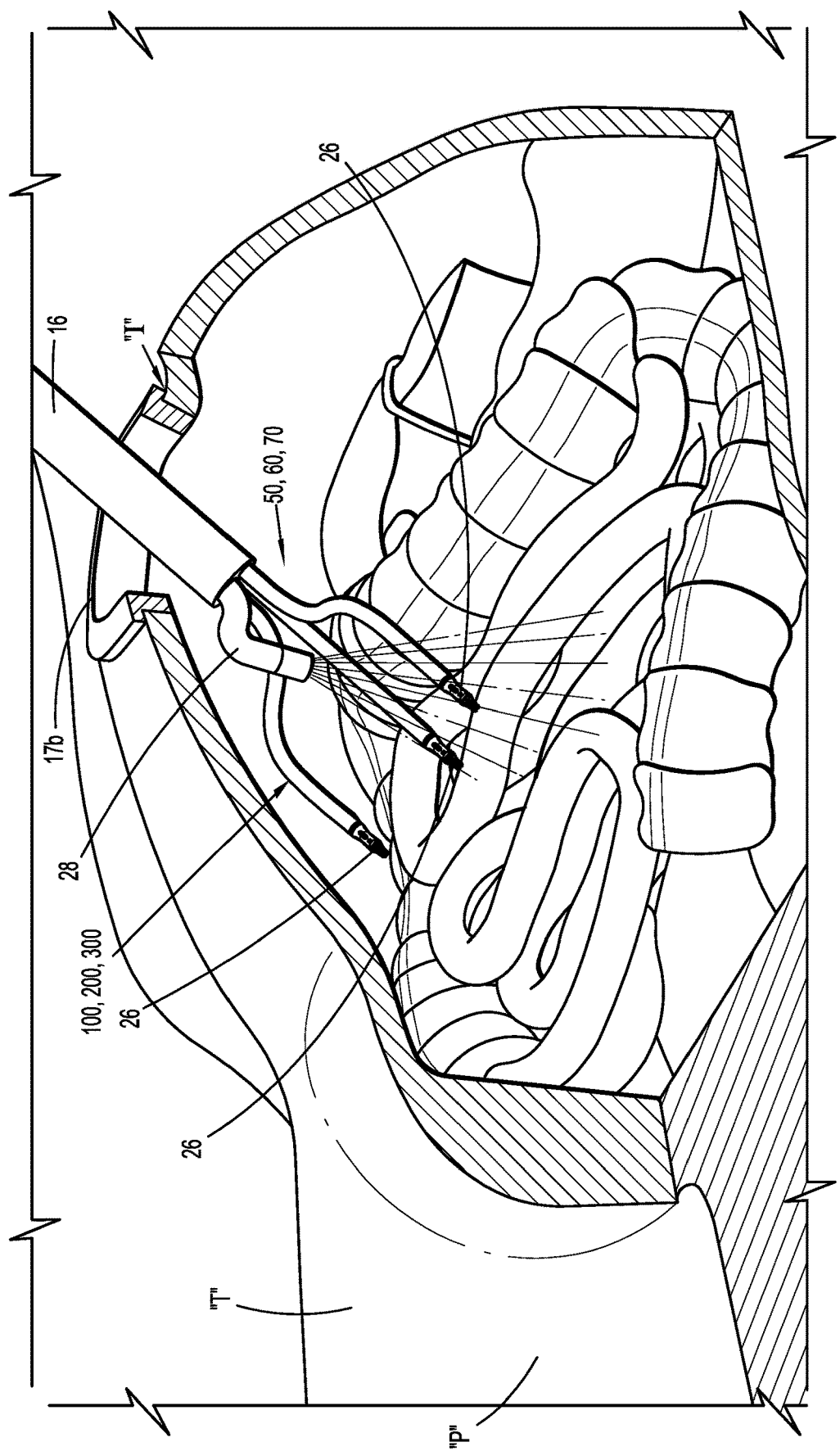
Figure 4:
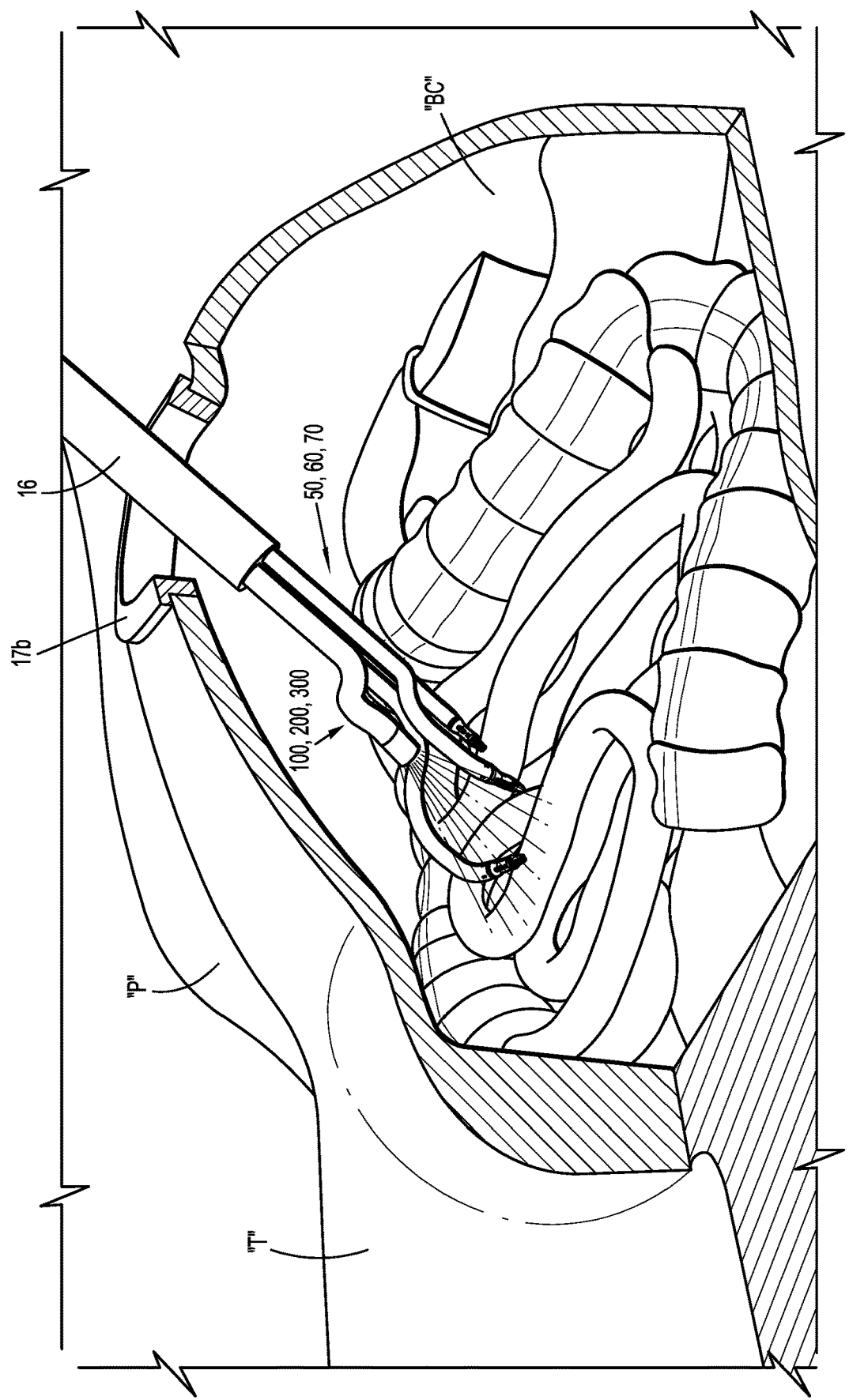

Aspects of this disclosure are described in detail with reference to the drawings, in which like reference numerals designate identical or corresponding elements in each of the several views. As used herein, the term "distal" refers to that portion of structure farther from the user, while the term "proximal" refers to that portion of structure, closer to the user. As used herein, the term "clinician" refers to a doctor, nurse, or other care provider and may include support personnel and/or equipment operators.

In the following description, well-known functions or constructions are not described in detail to avoid obscuring the present disclosure in unnecessary detail.

Robotic surgical systems have been used in minimally invasive medical procedures and can include robotic arm assemblies. Such procedures may be referred to as what is commonly referred to as "Telesurgery." Some robotic arm assemblies include one or more robot arms to which surgical instruments can be coupled. Such surgical instruments include, for example, endoscopes, electrosurgical forceps, cutting instruments, staplers, graspers, electrocautery devices, or any other endoscopic or open surgical devices. Prior to or during use of the robotic surgical system, various surgical instruments can be selected and connected to the robot arms for selectively actuating end effectors of the connected surgical instruments.

With reference to FIGS. 1-4, a robotic surgical system is shown generally at 10. Robotic surgical system 10 employs various robotic elements to assist the clinician and allow remote operation (or partial remote operation) of surgical instruments 100, 200, 300 of surgical instrument systems 50, 60, 70 of robotic surgical system 10. Various controllers, circuitry, robotic arms, gears, cams, pulleys, electric and mechanical motors, etc. may be employed for this purpose and may be designed with surgical system 10 to assist the clinician during an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

Robotic surgical system 10 includes a workstation 12 and an instrument cart 14. The instrument cart 14 includes one or more surgical instrument systems 50, 60, 70 mounted on a moveable drive unit 18 that houses an instrument drive assembly 20 for manipulating the surgical instrument systems 50, 60, 70 and/or independent surgical instruments 100, 200, 300 thereof with the assistance of, for example one or more computing devices or controllers. The surgical instruments 100, 200, 300 can include, for example, graspers or forceps 26, which may be electrosurgical, an endoscope 28, and/or any other suitable instrument that can be driven by one or more associated tool drives (not shown) of instrument drive assembly 20. For example, besides graspers 26 and endoscope 28, the one or more surgical instruments 100, 200, 300 can include dexterous tools, such as grippers, needle drivers, staplers, dissectors, cutters, hooks, graspers, scissors, coagulators, irrigators, suction devices, that are used for performing a surgical procedure.

Each surgical instrument system 50, 60, 70 includes an insertion tube 16 defining a plurality of separate conduits, channels or lumens 16a therethrough that are configured to receive, for instance, the surgical instruments 100, 200, 300 for accessing a body cavity "BC" of a patient "P." In other aspects, the insertion tube 16 may define a single conduit, channel or lumen therethrough that is configured to receive, for instance, the surgical instruments 100, 200, 300 for accessing a body cavity "BC" of a patient "P." In particular, the insertion tube 16 can be inserted through an incision "I" and/or access device 17 (e.g., a surgical portal, which may include or more seals to facilitate sealed insertion through tissue "T" of the patient "P") and into the body cavity "BC" of the patient "P"). With insertion tube 16 positioned in the patient "P," the surgical instruments 100, 200, 300 can be advanced through insertion tube 16 into the body cavity "BC" of the patient "P." Further, the workstation 12 includes an input device 22 for use by a clinician for controlling the insertion tube 16 and the various surgical instrument systems 50, 60, 70 (and surgical instruments 100, 200, 300 thereof) via the instrument drive assembly 20 to perform surgical operations on the patient "P" while the patient "P" is supported on a surgical table 24, for example. Input device 22 is configured to receive input from the clinician and produces input signals. Input device 22 may also be configured to generate feedback to the clinician. The feedback can be visual, auditory, haptic, or the like.

The workstation 12 can further include computing devices and/or controllers such as a master processor circuit 22a in communication with the input device 22 for receiving the input signals and generating control signals for controlling the robotic surgical system 10, which can be transmitted to the instrument cart 14 via an interface cable 22b. In some cases, transmission can be wireless and interface cable 22b may not be present. The input device 22 can include right and left-hand controls (not shown) and/or foot pedals (not shown), which are moved/operated to produce input signals at the input device 22 and/or to control robotic surgical system 10. The instrument cart 14 can include a slave processor circuit 20a that receives and the control signals from the master processor circuit 22a and produces slave control signals operable to control the various surgical instrument systems 50, 60, 70 (and surgical instruments 100, 200, 300 thereof) during a surgical procedure. The workstation 12 can also include a user interface, such as a display (not shown) in communication with the master processor circuit 22a for displaying information (such as, body cavity images) for a region or site of interest (for example, a surgical site, a body cavity, or the like) and other information to a clinician. While both master and slave processor circuits are illustrated, in other aspects, a single processor circuit may be used to perform both master and slave functions.

Turning now to FIGS. 5-17, surgical instrument system 50 of robotic surgical system 10 includes insertion tube 16 and a plurality of surgical instruments 100 that is insertable through insertion tube 16. Although only three surgical instruments 100 are shown, surgical instrument system 50 can include any number and/or type of surgical instruments such as graspers 26 and endoscope 28 as noted above.

As seen in FIGS. 6 and 7, surgical instrument 100 of surgical instrument system 50 defines a longitudinal axis "L" and includes an instrument cassette assembly 102 on a proximal end portion thereof, an elongated shaft assembly 104 that extends distally from instrument cassette assembly 102, and an end effector 106 supported on a distal end portion of elongated shaft assembly 104. End effector 106 is actuatable by instrument cassette assembly 102 for effectuating a surgical procedure. Indeed, actuating end effector 106 can cause end effector 106 to, for example, articulate, pivot, clamp, rotate, etc. relative to the longitudinal axis "L" of surgical instrument 100 for repositioning end effector 106 and/or for treating tissue "T" of the patient "P" as noted above (see FIGS. 2-4).

With reference to FIG. 8, instrument cassette assembly 102 of surgical instrument 100 includes a cassette housing 108 that supports an actuator system 110 and is coupled to elongated shaft assembly 104. Actuator system 110 includes a plurality of cable actuator assemblies 112, a rotation actuator assembly 114, and an axial actuator assembly 116.

As seen in FIG. 9, cassette housing 108 of instrument cassette assembly 102 includes a first housing 108a, a second housing 108b, and a lid 108c that couple together to support the actuator system 110 therein and secure cassette housing 108 to elongated shaft assembly 104.

Figure 5:
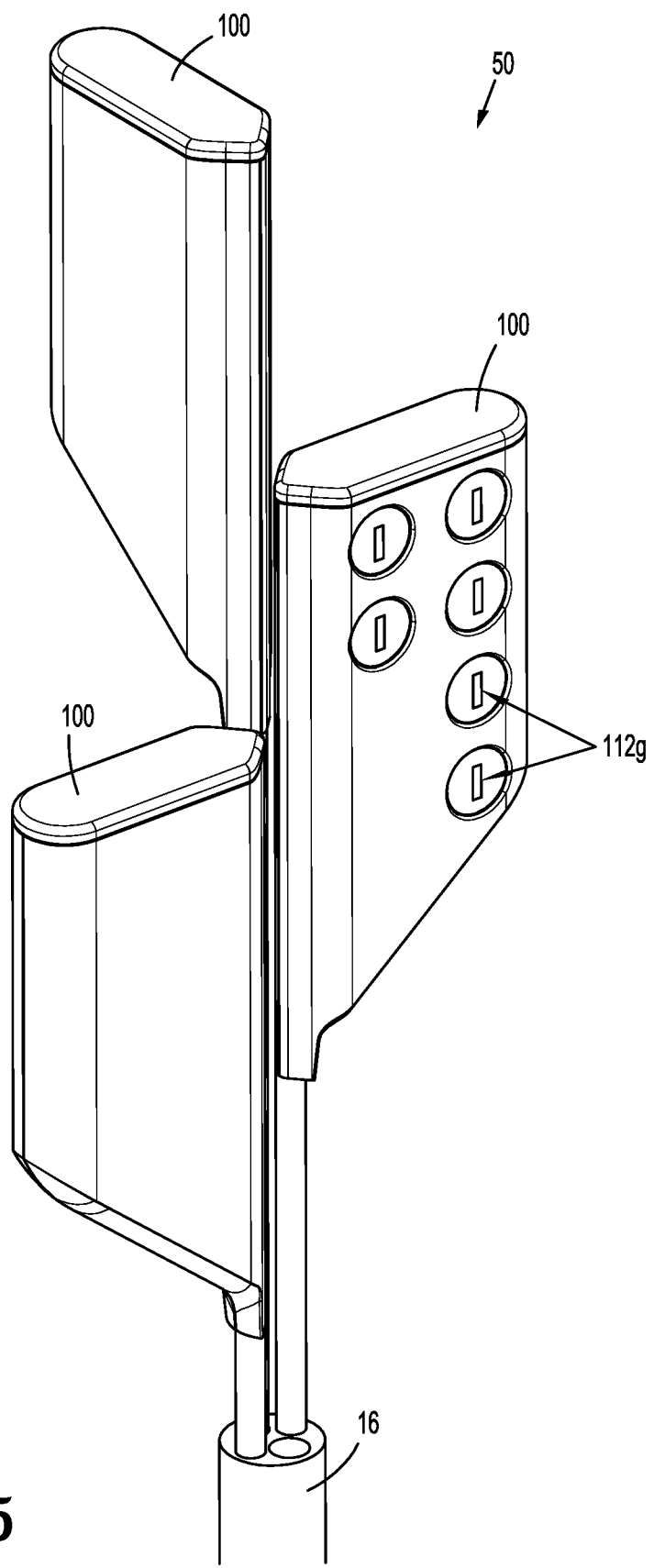
FIG. 5 is an enlarged, perspective view of proximal portions of surgical instruments of one surgical instrument system of the robotic surgical system of FIG. 1.
Figure 11:
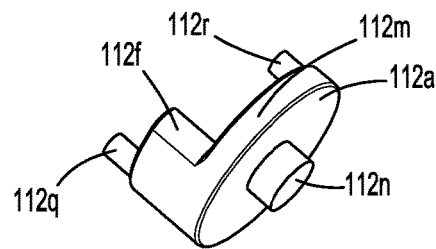
FIG. 11 is a perspective view of a crank of a cable actuator assembly of the actuator system of FIG. 10.
Figure 10:
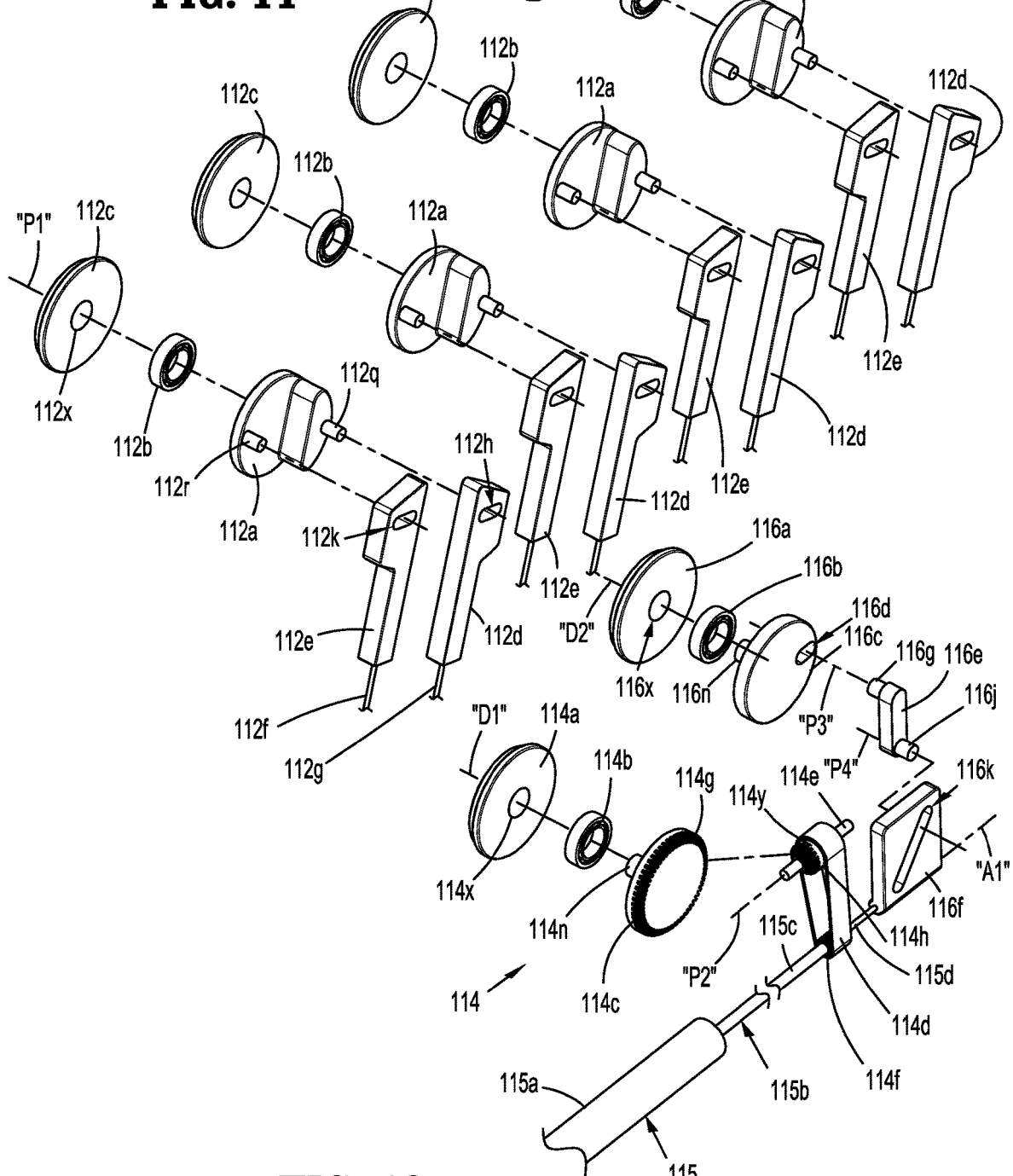
FIG. 10 is a perspective view, with parts separated, of an actuator system of the instrument cassette assembly of FIG. 9.
Figure 12:
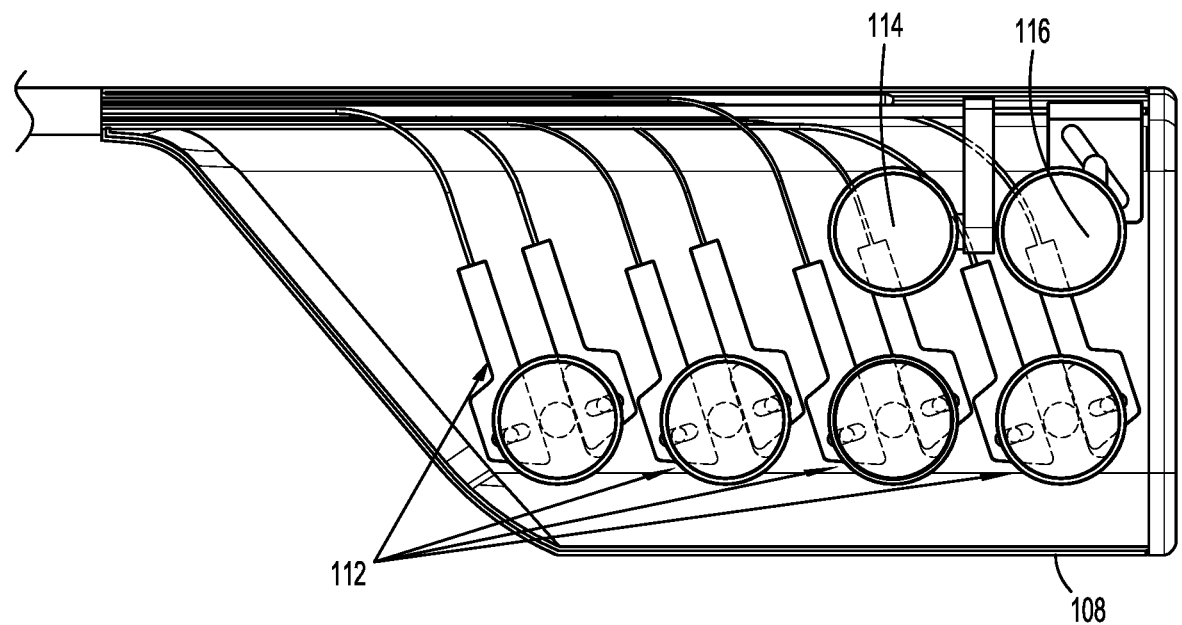
FIGS. 12 and 13 are progressive views illustrating cable actuator assemblies of the actuator system of FIG. 10 being actuated.

With reference to FIGS. 10-13, each cable actuator assembly 112 of the actuator system 110 of instrument cassette assembly 102 includes a crank 112a that supports a bearing 112b and a driver 112c on a first end of the crank 112a. The crank 112a further supports a first slider 112d and a second slider 112e on a second end of the crank 112a. The first slider 112d is supported on a first side of the crank 112a and the second slider 112e is supported on a second side of the crank 112 opposite to the first side of the crank 112a. The first slider 112d supports a first cable 112g and the second slider 112e supports a second cable 112f The first slider 112d defines a first slot 112h and the second slider 112e defines a second slot 112k. The crank 112a includes a plate 112m having a central bearing prong 112n extending from the first end thereof. The central bearing prong 112n is received through the bearing 112b and is nonrotatably coupled to driver 112c of the cable actuator assembly 112. In aspects, central bearing prong 112n of the crank 112a can be keyed to a bore 112x defined in driver 112c on the second end of driver 112c to enable crank 112a and driver 112c to be press-fit together. Central bearing prong 112n of crank 112a and bore 112x of driver 112c can have any suitable counterpart geometry (e.g., square, triangle, star, chamfer, bevel, fillet, edge, groove, etc.) to enable driver 112c to impart rotational driving force to crank 112a via the nonrotatable coupling of driver 112c and crank 112a. In aspects, driver 112c can be secured to crank 112a via any suitable technique such as sonic welding, adhesive, fastener, snap-fit, etc., or combinations thereof such that driver 112c can rotate crank 112a about a central pivot axis "P1." Briefly, as seen in FIG. 5, driver 112c defines a drive slot 112y therein to receive rotational drive force from moveable drive unit 18.

Figure 13:
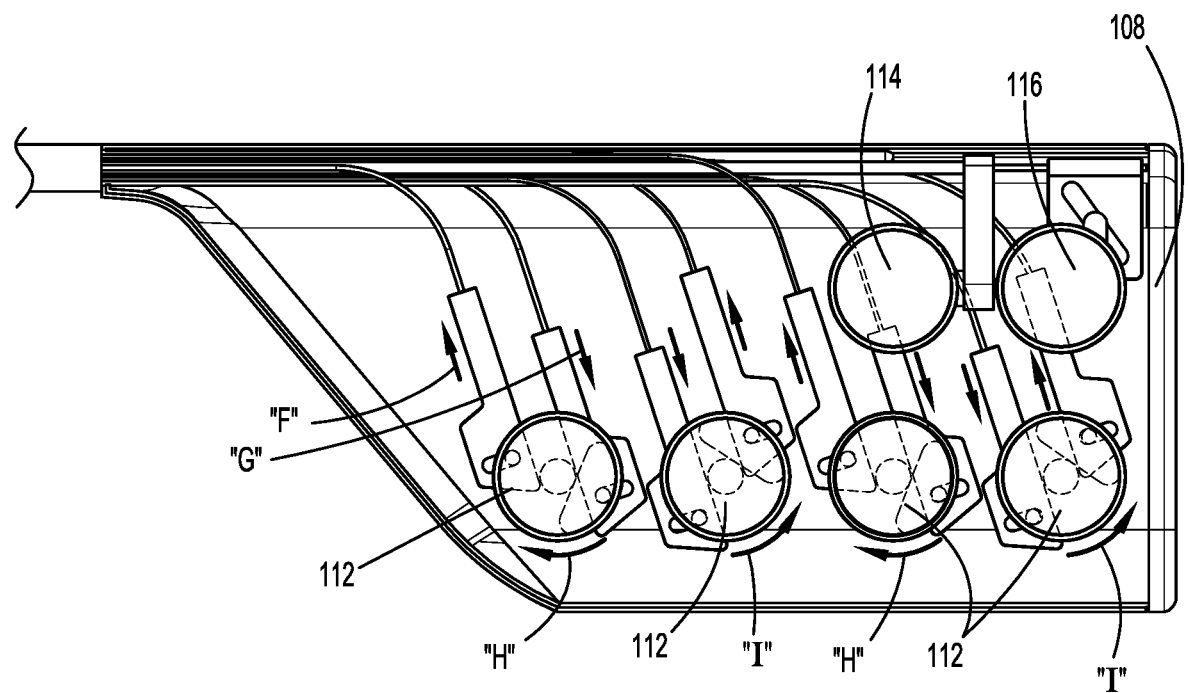

With continued reference to reference to FIGS. 10-13, the plate 112m of crank 112a further includes a shoulder 112p having a first finger 112q extending from a second side of the plate 112m, and a second finger 112r extending from the first side of the plate 112m and recessed from the first finger 112q. The first and second fingers 112q, 112r of crank 112a are received within first and second slots 112h, 112k of the respective first and second sliders 112d, 112e. Crank 112a is configured to move (e.g., translation or linear movement, which may be reciprocating movement) first and second sliders 112d, 112e relative to one another, as indicated by arrows "F" and "G" as shown in FIG. 13, when crank 112a rotates in clockwise and/or counterclockwise directions as indicated by arrows "H" and "I." Linear movement of first and second sliders 112d, 112e causes first and second cables 112f, 112g to actuate (e.g., articulate, elevate, fire, clamp, etc. end effector 106 and/or jaw members thereof). Each cable actuator assembly 112 of the actuator system 110 may move independent and/or dependent of one or more of the other cable actuator assemblies 112 to actuate/operate the end effector 106 as desired.

Referring to FIGS. 10-14, rotation actuator assembly 114 of the actuator system 110 includes a driver 114a, a bearing 114b, a drive wheel 114c, a belt 114d, a belt drive shaft 114e, and a belt drum 114f. Drive wheel 114c of rotation actuator assembly 114 includes a first bevel gear 114g. Belt drive shaft 114e of rotation actuator assembly 114 includes a second bevel gear 114h that is transverse to first bevel gear 114g and positioned to meshingly engage first bevel gear 114g of drive wheel 114c. Belt drive shaft 114e further includes a drum gear 114y supported adjacent to second bevel gear 114h and positioned to enable belt 114d to slide therealong as belt 114d rotates about belt drive shaft 114e. First bevel gear 114g is configured to rotate second bevel gear 114h about pin axis "P2," as indicated by arrow "R1," when first bevel gear 114g rotates about drive axis "D1," as indicated by arrow "R2." Rotation of second bevel gear 114h about drive axis "D1," as indicated by arrow "R1," causes belt 114d to rotate about belt drive shaft 114e and belt drum 114f, as indicated by arrow "R3."

Belt drum 114f of rotation actuator assembly 114 is connected to a shaft assembly 115 including an outer shaft 115a and an inner shaft assembly 115b such that rotation of belt 114d causes belt drum 114f to rotate about shaft axis "A1" defined by shaft assembly 115, as indicated by arrow "R4." Inner shaft assembly 115b includes a first inner shaft 115c and a second inner shaft 115d that is slidably advanceable through first inner shaft 115c along shaft axis "A1" of shaft assembly 115. First inner shaft 115c supports belt drum 114f on a first end thereof with the second end of first inner shaft 115c coupled to end effector 106 (FIG. 7) for imparting rotational movement/force on end effector 106. Belt drum 114f is positioned to rotate about shaft axis "A1" as belt 114d rotates about belt drum 114f. Further, like driver 112c of cable actuator assembly 112, driver 114a of rotation actuator assembly 114 includes a drive slot 112y on a first end thereof. Likewise, driver 114a of rotation actuator assembly 114 is nonrotatably coupled to drive wheel 114c, for example, via a central bearing prong 114n extending from a first end of drive wheel 114c. Central bearing prong 114n supports bearing 114b and may be mechanically coupled to the second end of driver 114a via a bore 114x of driver 114a (e.g., press-fit) and/or via sonic welding, adhesive, fastener, etc., or combinations thereof such that driver 114a imparts rotational movement on drive wheel 114c about drive axis "D1" as driver 114a rotates about drive axis "D1."

Referring to FIGS. 10-17, axial actuator assembly 116 of actuator system 110 includes a driver 116a, a bearing 116b, a drive disc 116c defining an elongated pin notch 116d, a drive arm 116e coupled to drive disc 116c, and a drive plate 116f coupled to drive arm 116e. Drive arm 116e includes a first pin 116g on a first end thereof that is slidably and rotatably received within elongated pin notch 116d of drive disc 116c to enable rotation of drive arm 116e about pivot axis "P3" defined through first pin 116g. Drive arm 116e further includes a second pin 116j on a second end thereof that is slidably and rotatably received within a pin slot 116k defined through drive plate 116f and disposed at an acute angle (e.g., 45 degrees) relative to shaft axis "A1." Drive arm 116e is also configured to pivot about pin axis "P4" defined through second pin 116j as second pin 116j slides through pin slot 116k of drive plate 116f. Further, like driver 112c of cable actuator assembly 112, driver 116a of axial actuator assembly 116 includes a drive slot 112y on a first end thereof. Likewise, driver 116a of axial actuator assembly 116 is nonrotatably coupled to drive disc 116c, for example, via a central bearing prong 116n extending from a first end of drive disc 116c. Central bearing prong 116n supports bearing 116b and may be mechanically coupled to the second end of driver 116a via a bore 116x of driver 116a (e.g., press-fit) and/or via sonic welding, adhesive, fastener, etc., or combinations thereof such that driver 116a imparts rotational movement on drive disc 116c about drive axis "D2" of axial actuator assembly 116 as driver 116a rotates about drive axis "D2."

Figure 15:
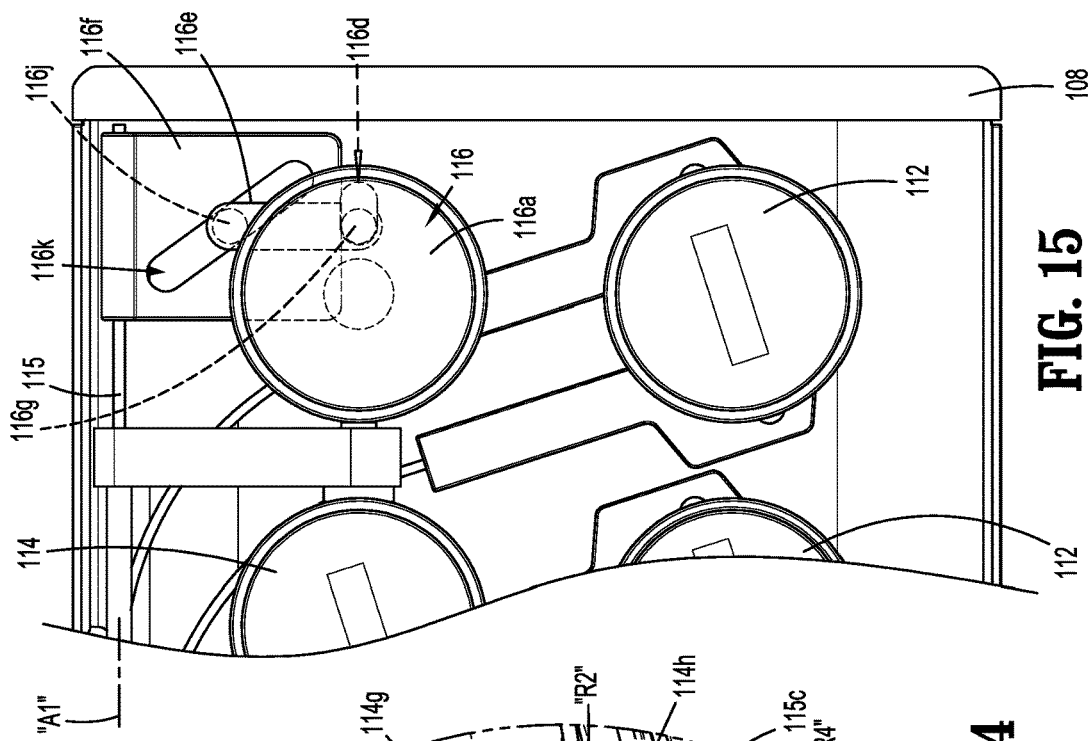
FIGS. 15-17 are progressive views illustrating an axial actuator assembly of the actuator system of FIG. 10 being actuated.
Figure 14:
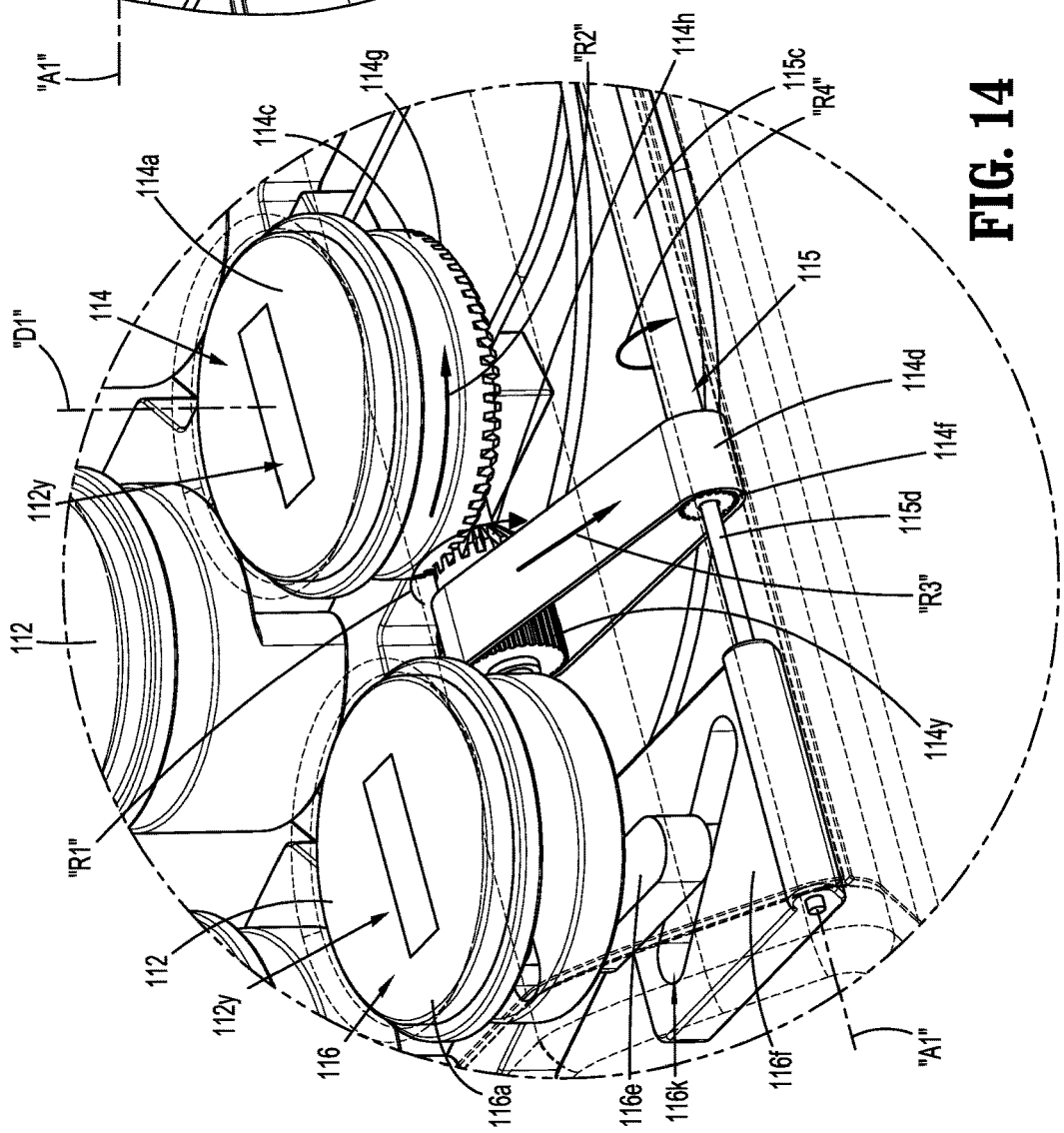
FIG. 14 is an enlarged view of the indicated area of detail shown in FIG. 8 and illustrating a rotation actuator assembly of the actuator system of FIG. 10 being actuated.
Figure 17:
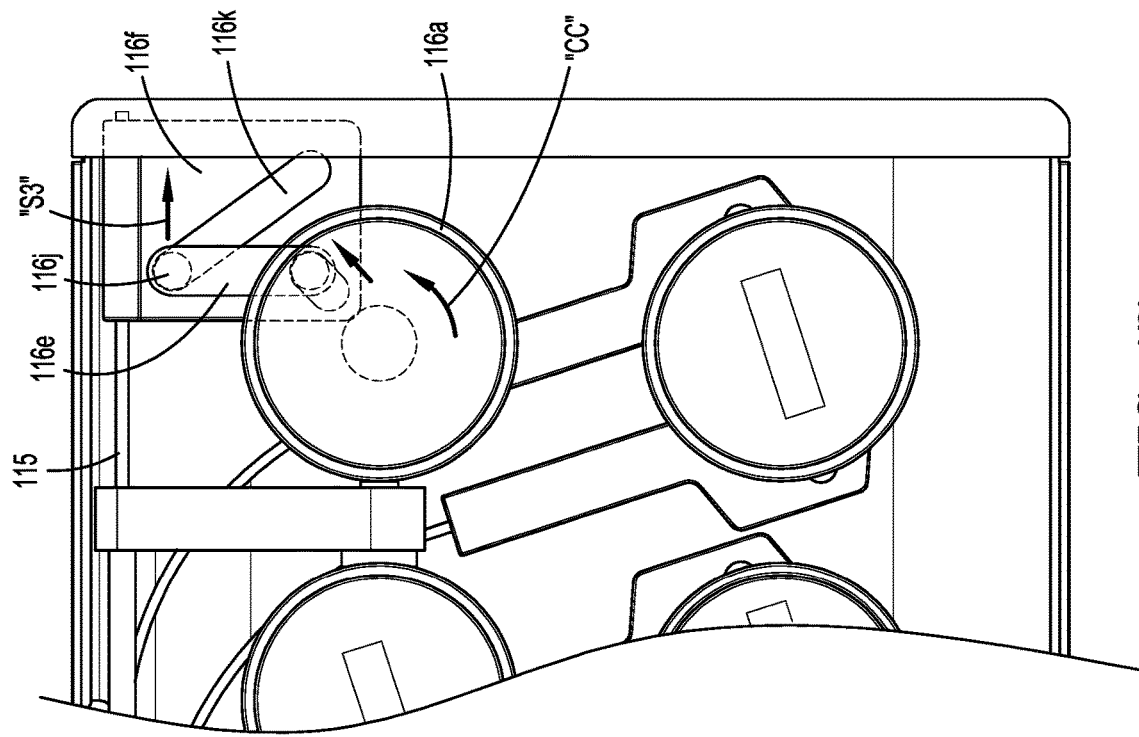
Figure 16:
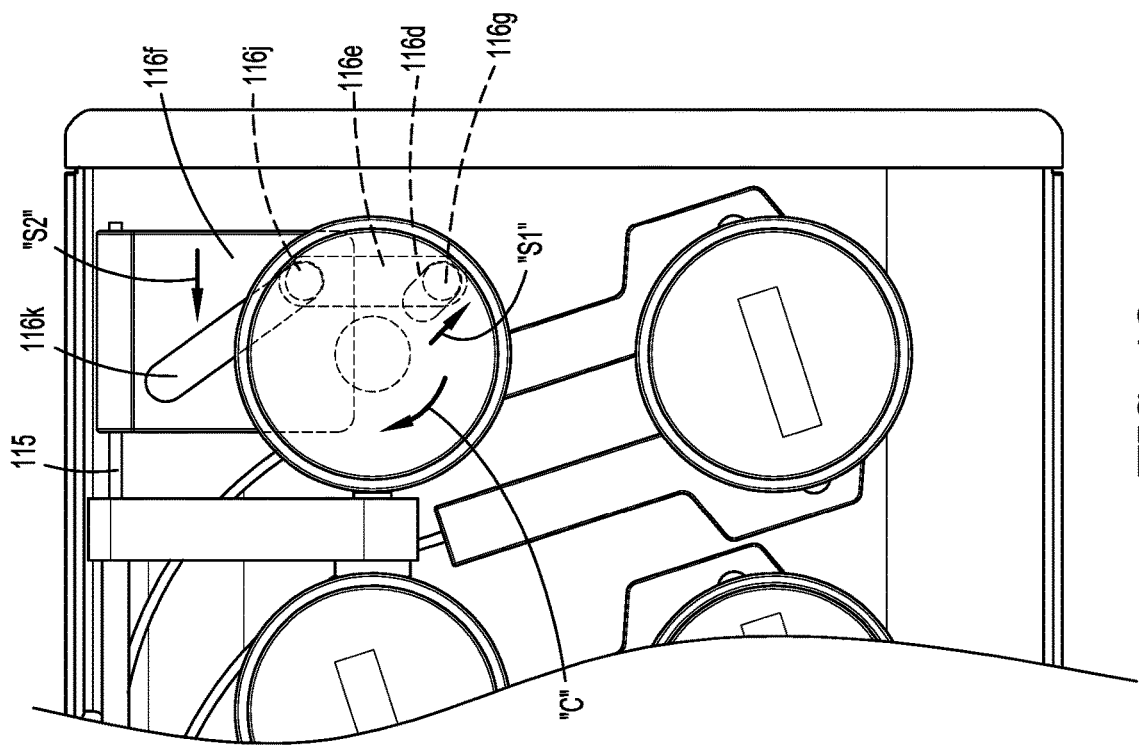

As seen in FIGS. 15-17, axial actuator assembly 116 of actuator system 110 is positioned to move between an intermediate position (FIG. 15), a retracted position (FIG. 16), and an extended position (FIG. 17). In the intermediate position, drive arm 116e is parallel to belt 114d and orthogonal to shaft axis "A1" with first pin 116g supported on a first side of elongated pin notch 116d and second pin 116j substantially centered along pin slot 116k of drive plate 116f. Rotation of driver 116a in a first direction (e.g., clockwise), as indicated by arrow "C," causes first pin 116g of drive arm 116e to slide to a second side (e.g., proximally) of elongated pin notch 116d, as indicated by arrow "S1." Rotation of driver 116a in the first direction also causes second pin 116j of drive arm 116e to slide to a first side of pin slot 116k, such that drive plate 116f is urged toward the extended position (e.g., distally), as indicated by arrow "S2," to impart distal axial movement to shaft assembly 115 and distal axial force and/or movement to end effector 106. Rotation of driver 116a in a second direction (e.g., counterclockwise), as indicated by arrow "CC," causes second pin 116j of drive arm 116e to slide to a second side (e.g., distally) of pin slot 116k such that drive plate 116f is urged toward the retracted position (e.g., proximally), as indicated by arrow "S3" to impart proximal axial movement to shaft assembly 115 and proximal axial force and/or movement to end effector 106.

Turning now to FIGS. 18-27, surgical instrument system 60 of robotic surgical system 10 includes insertion tube 16 and a plurality of surgical instruments 200 that is insertable through insertion tube 16. Although only three surgical instruments 200 are shown, surgical instrument system 60 can include any number and/or type of surgical instruments such as graspers 26 and endoscope 28 as noted above.

Figure 18:
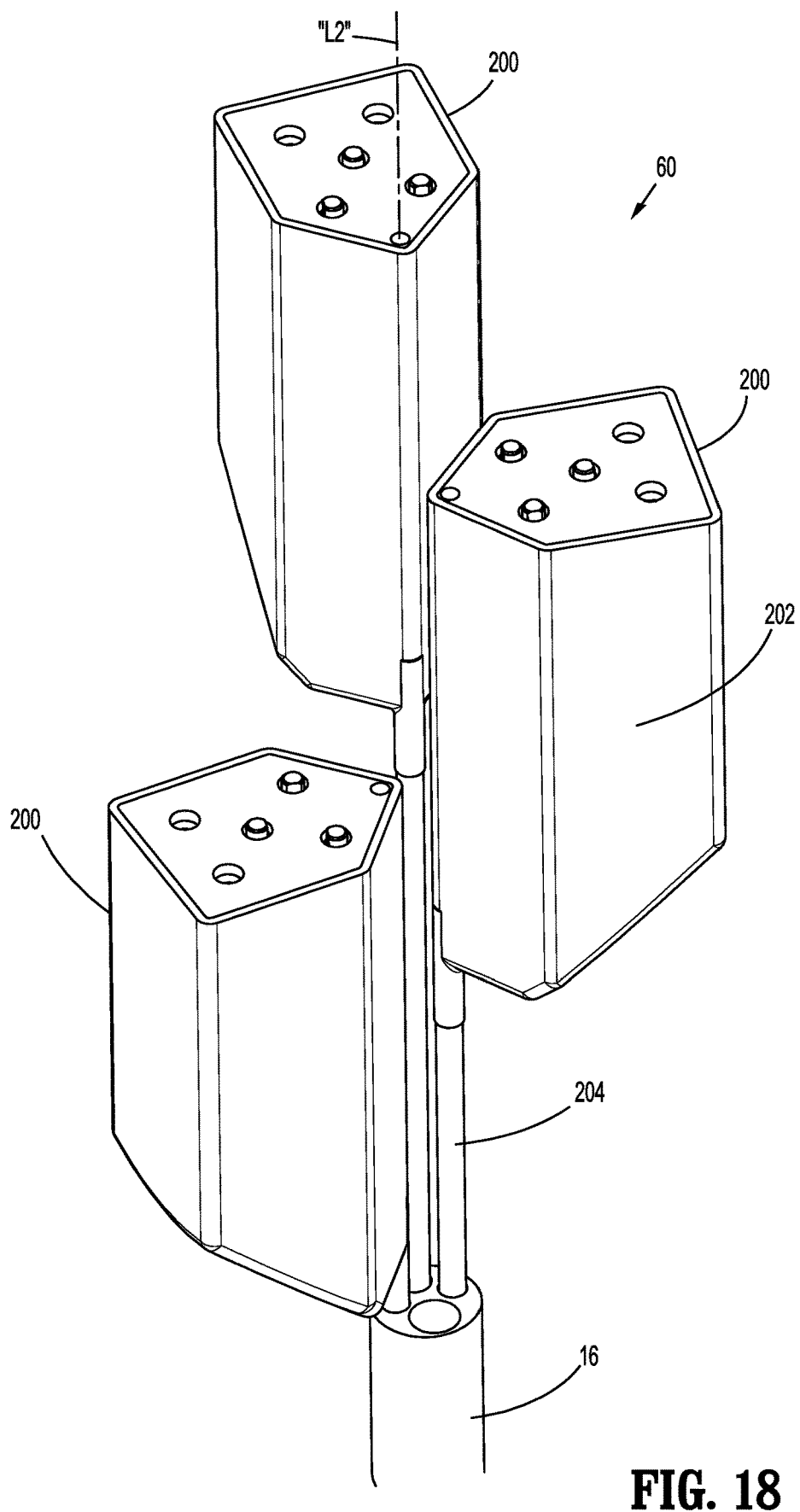
FIG. 18 is an enlarged, perspective view of proximal portions of surgical instruments of another surgical instrument system of the robotic surgical system of FIG. 1.
Figure 19:
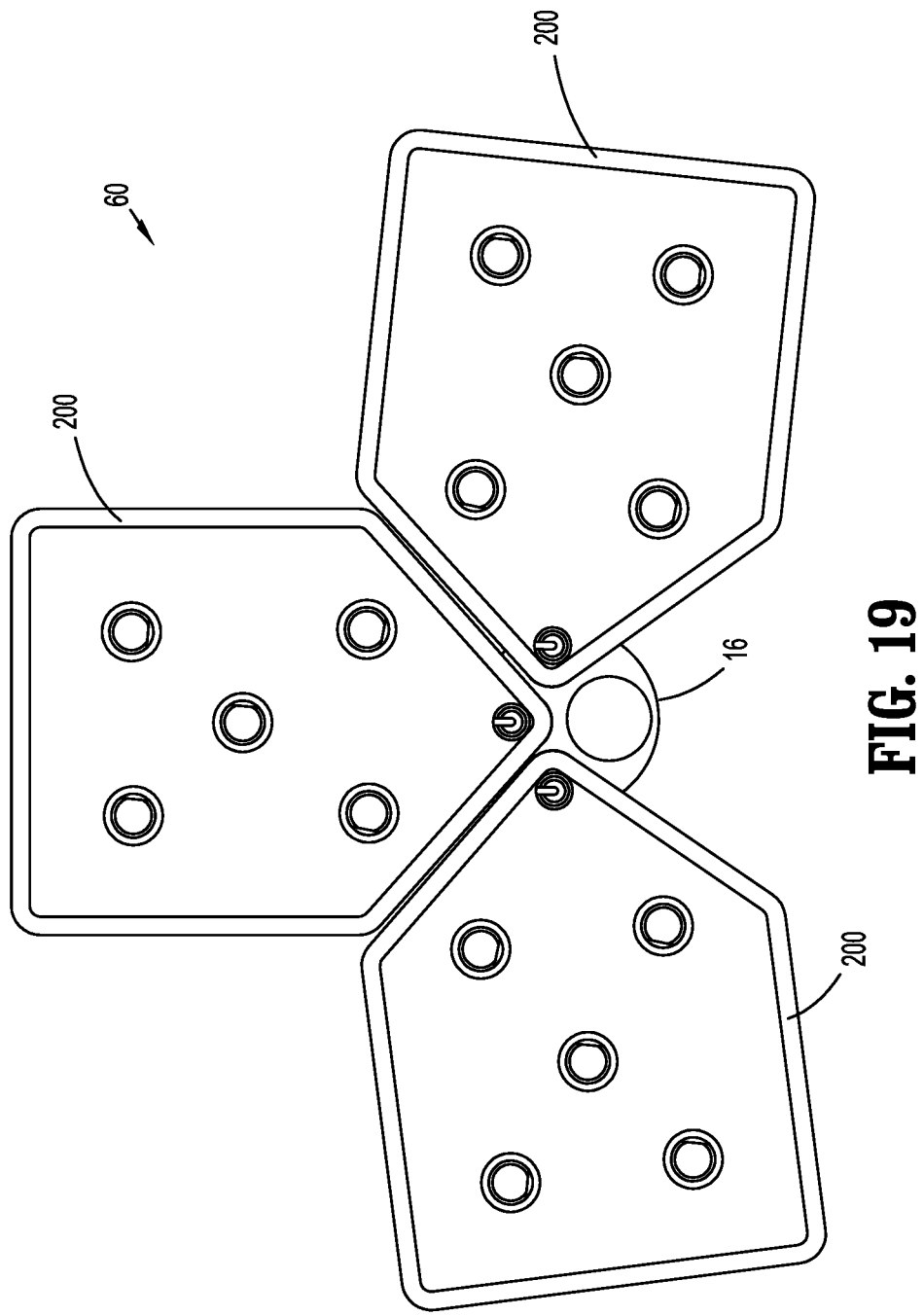
FIG. 19 is an enlarged top view of FIG. 18.

As seen in FIG. 18, surgical instrument 200 of surgical instrument system 60 defines a longitudinal axis "L2" and includes an instrument cassette assembly 202 on a proximal end portion thereof and an elongated shaft assembly 204 that extends from instrument cassette assembly 202 to an end effector 106 (FIG. 7) supported on a distal end portion of elongated shaft assembly 204. End effector 106 is actuatable by instrument cassette assembly 202 for effectuating a surgical procedure. Indeed, actuating end effector 106 can cause end effector 106 to, for example, articulate, pivot, clamp, rotate, etc. relative to the longitudinal axis "L2" of surgical instrument 200 for repositioning end effector 106 and/or for treating tissue "T" of the patient "P" as noted above (see FIGS. 2-4).

Figure 20:
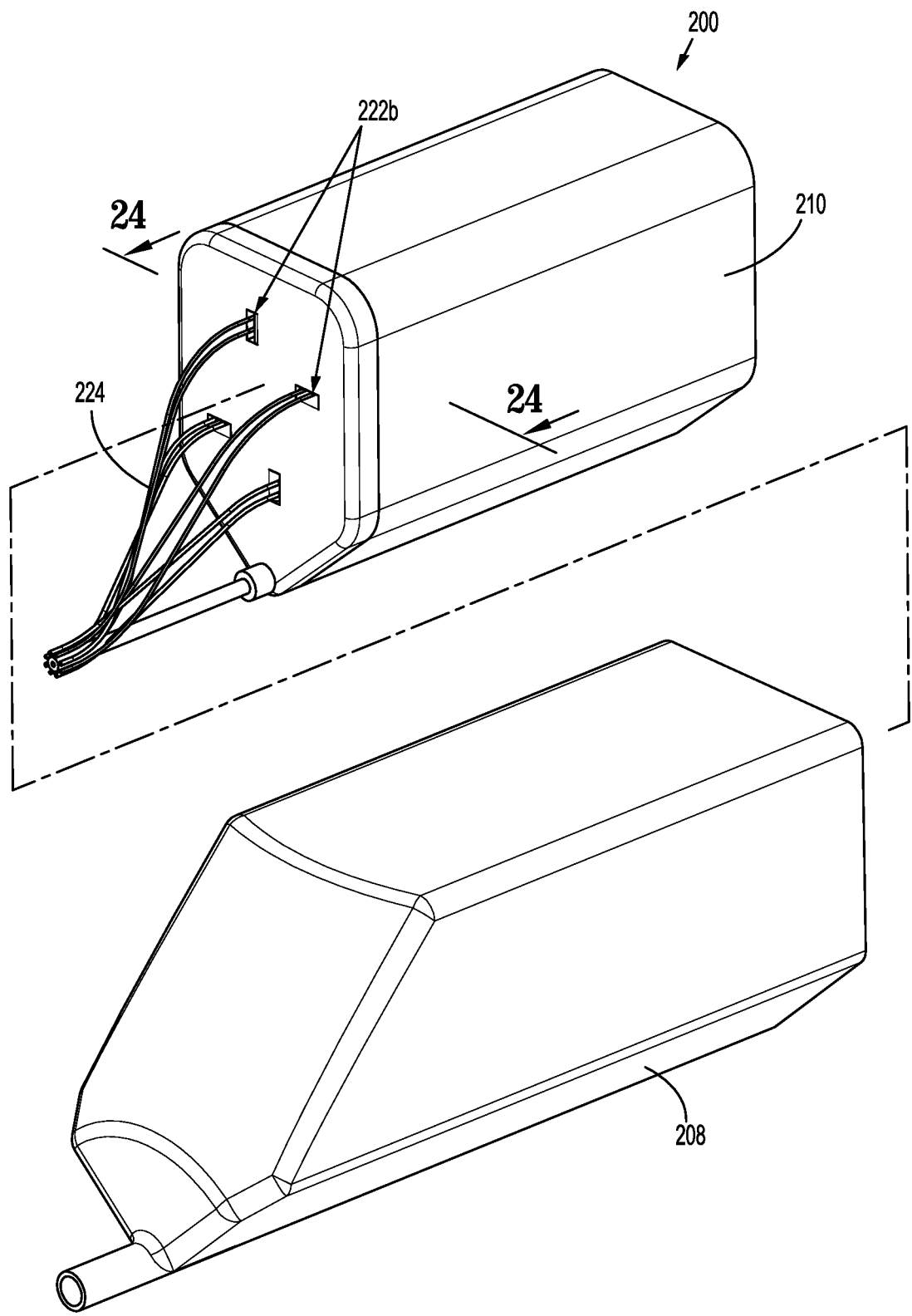
FIG. 20 is a perspective view, with parts separated, of another instrument cassette assembly of one of the surgical instruments of the surgical instrument system of FIG. 18, the instrument cassette assembly including an outer housing assembly and an inner housing assembly.
Figure 21:
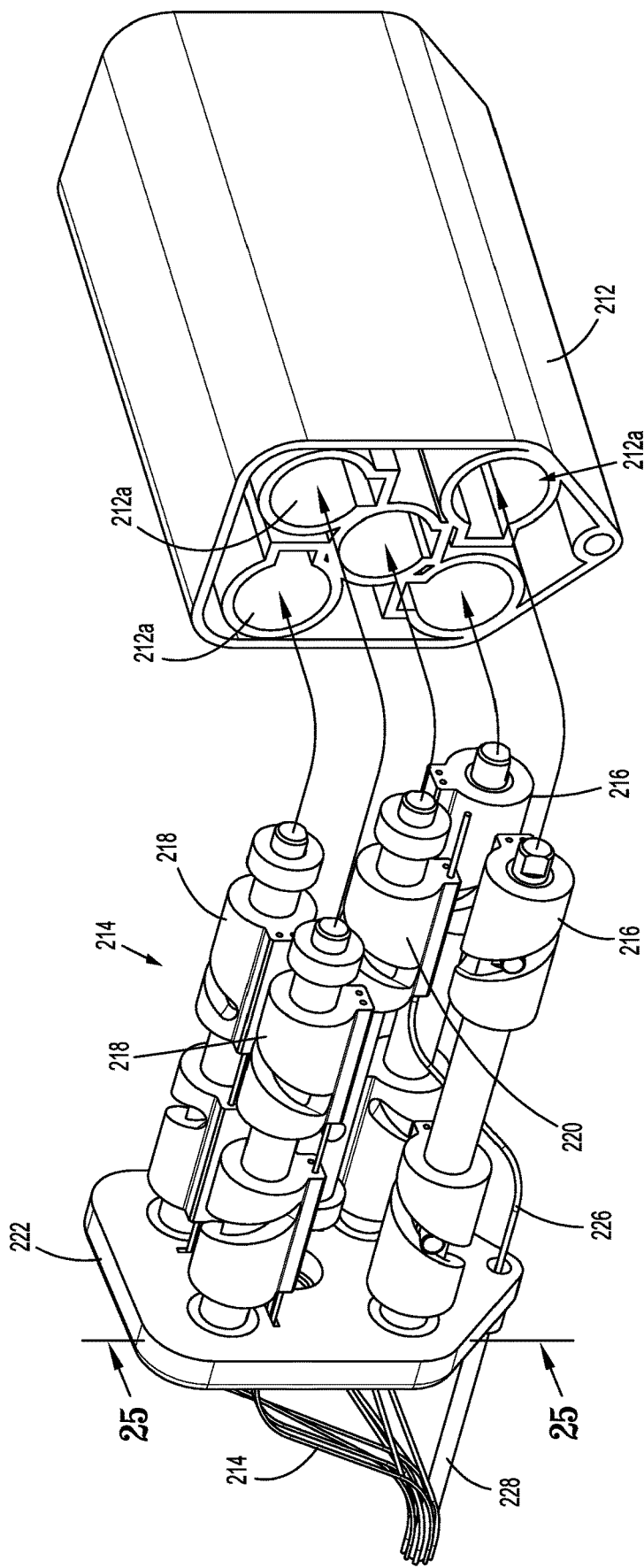
FIG. 21 is a perspective view, with parts separated, of the inner housing assembly of FIG. 20, the inner housing assembly including an actuator housing and an actuator assembly.
Figure 22:
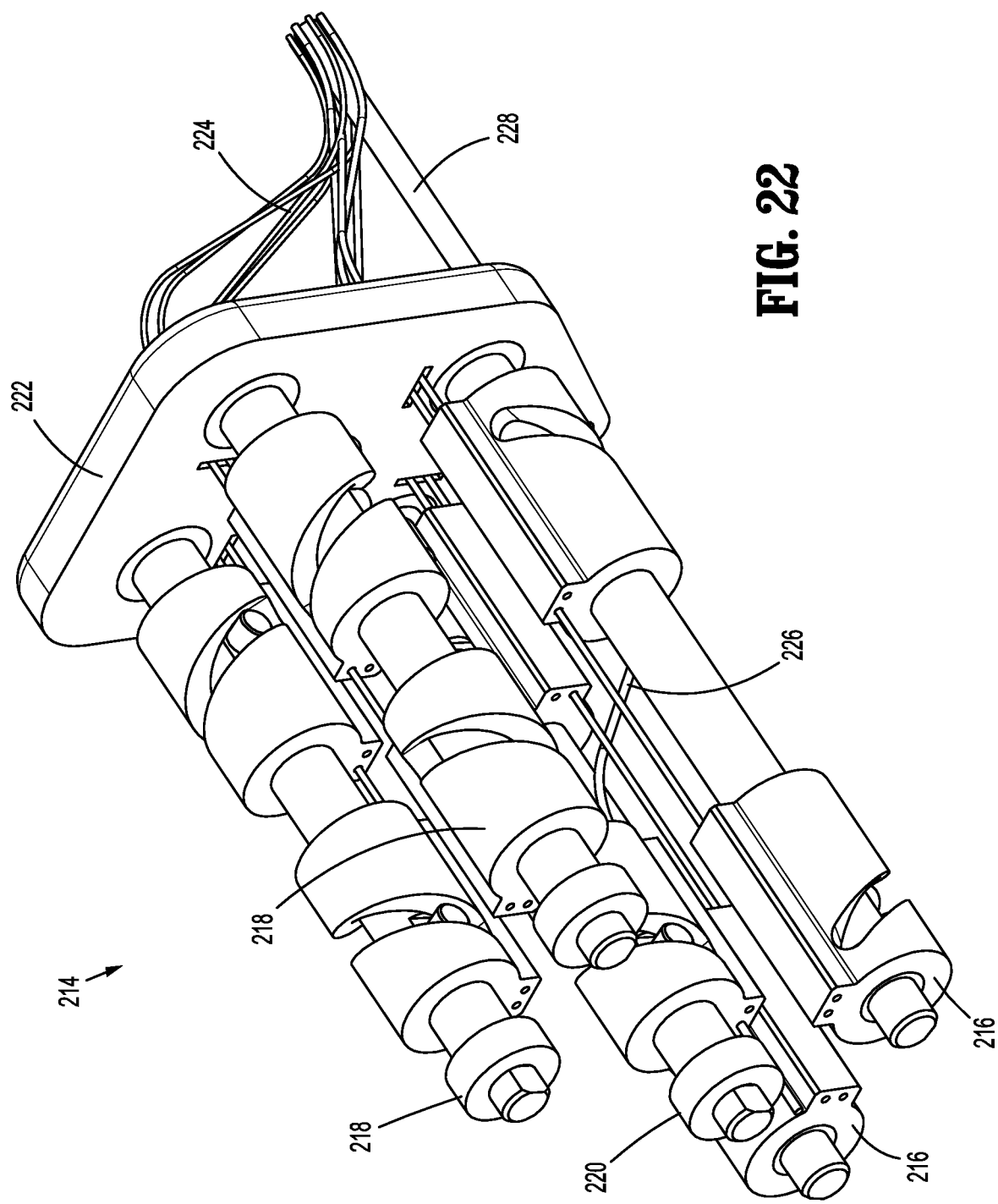
FIG. 22 is a perspective view of the actuator assembly of FIG. 21.
Figure 23:
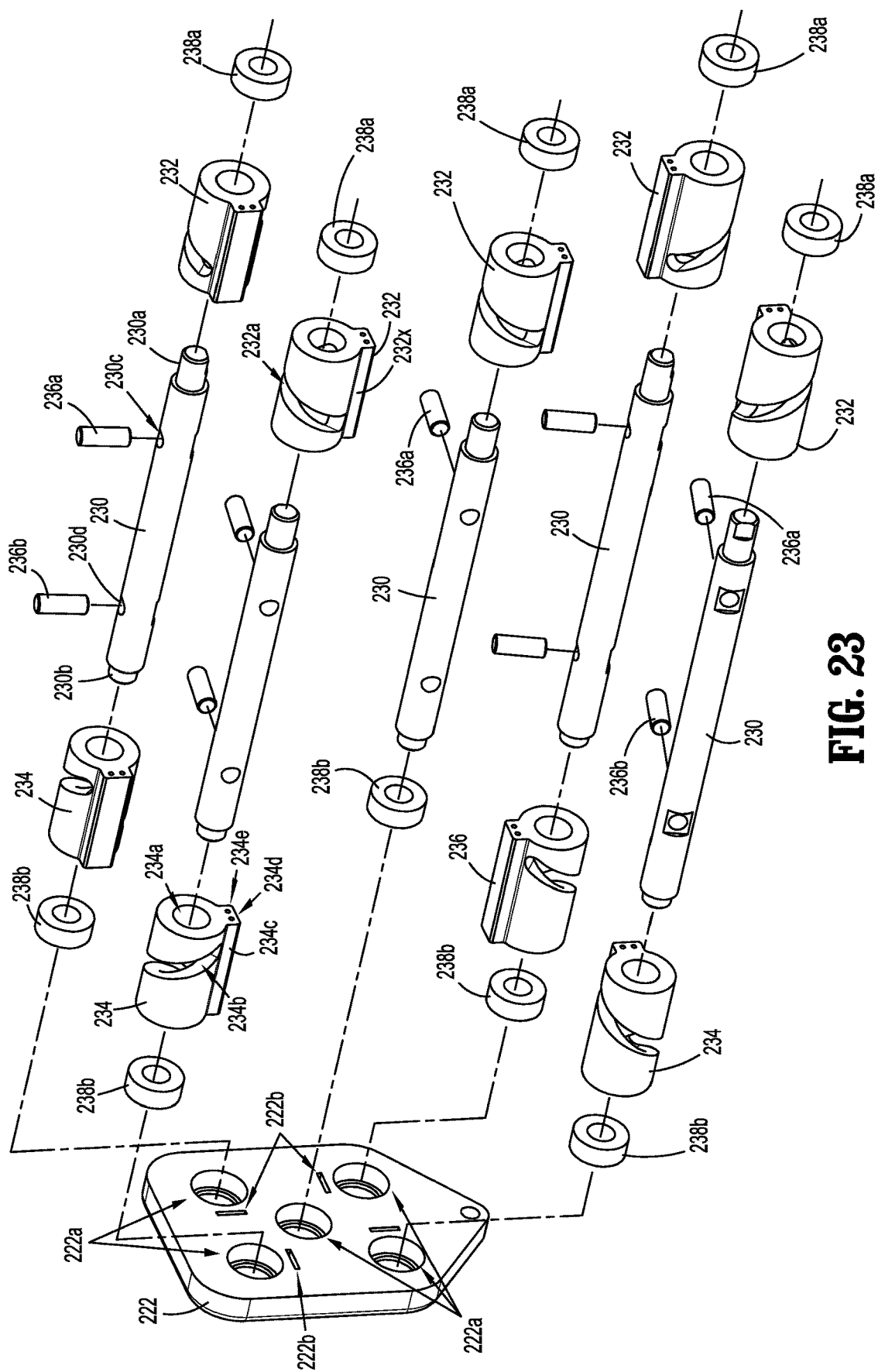
FIG. 23 is a perspective view, with parts separated, of the actuator assembly of FIG. 21, the actuator assembly shown with portions removed for clarity.
Figure 24:
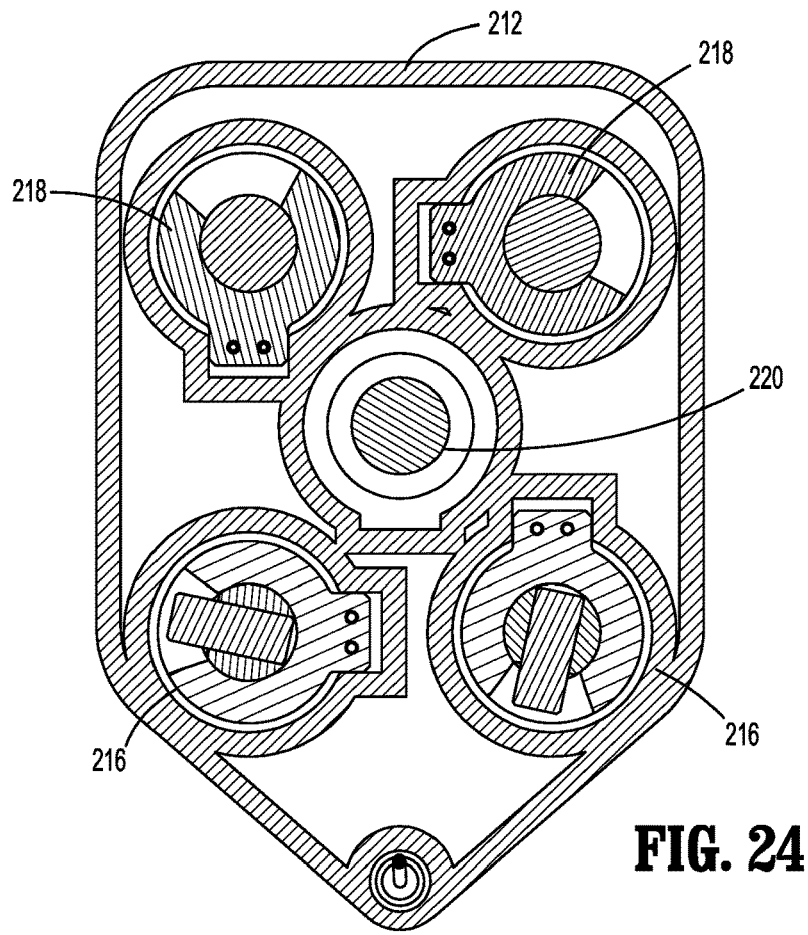
FIG. 24 is an enlarged, cross-sectional view as taken along section line 24-24 shown in FIG. 20.
Figure 25:
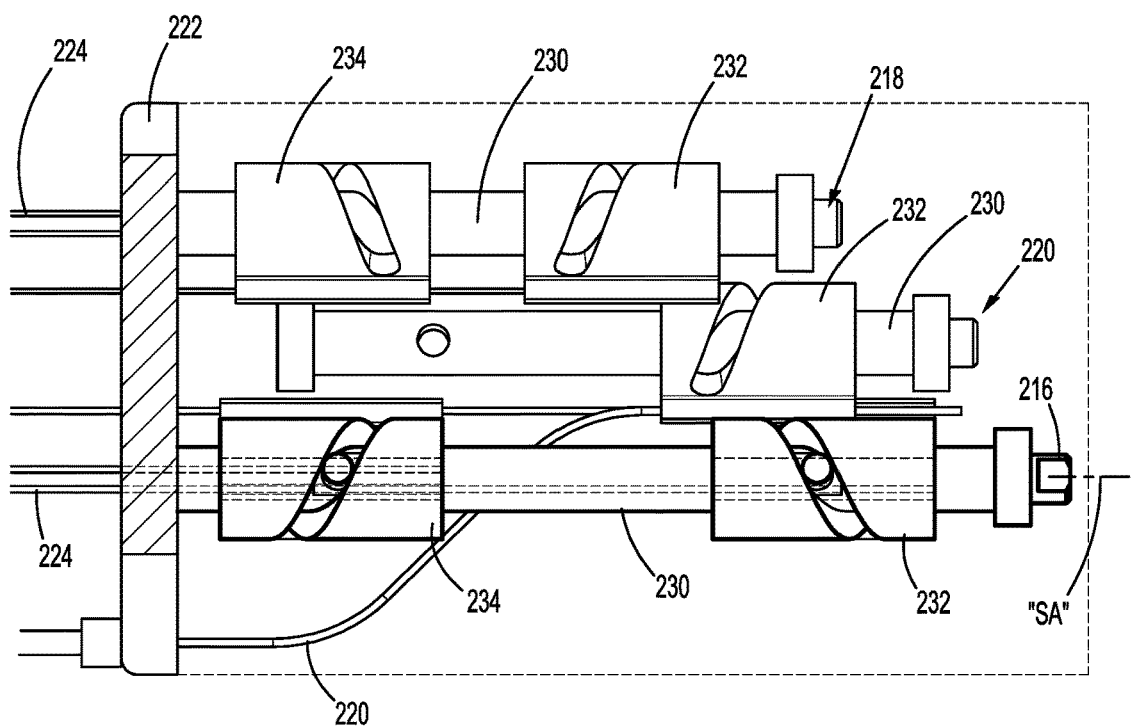
FIG. 25 is an enlarged, cross-sectional view as taken along section line 25-25 shown in FIG. 21.
Figure 26:
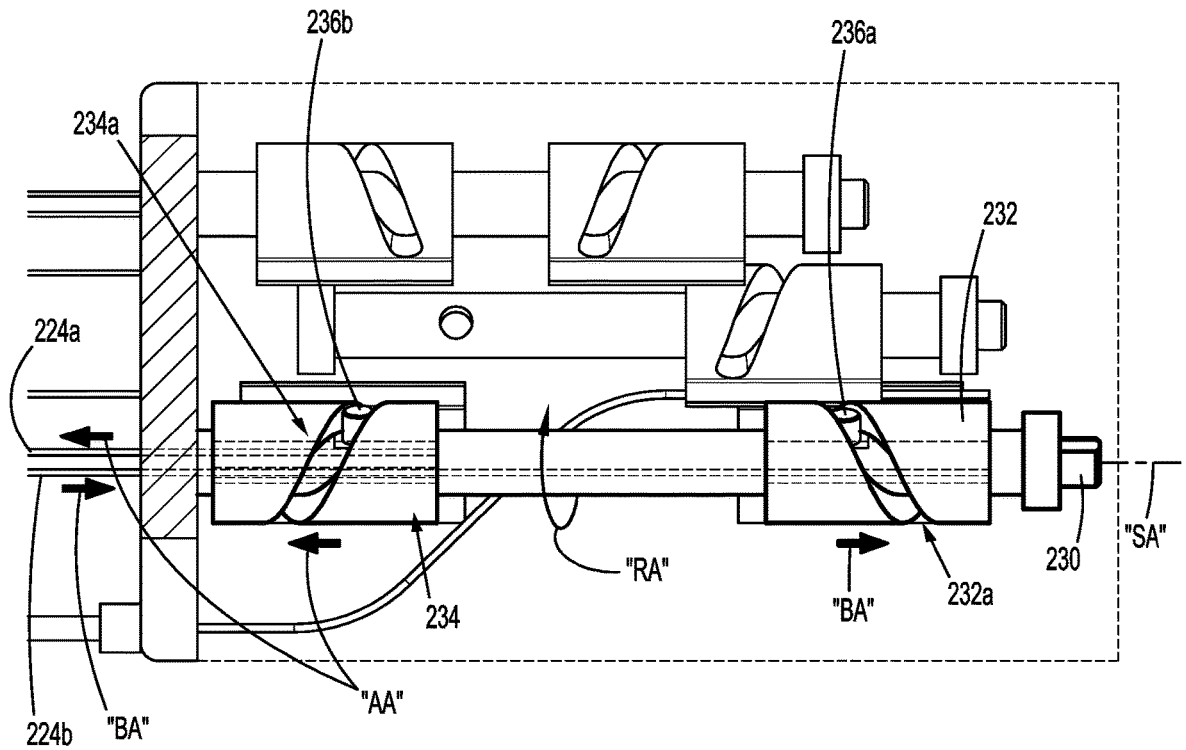
FIGS. 26 and 27 are progressive views illustrating the actuator assembly of FIG. 21 being actuated.
Figure 27:
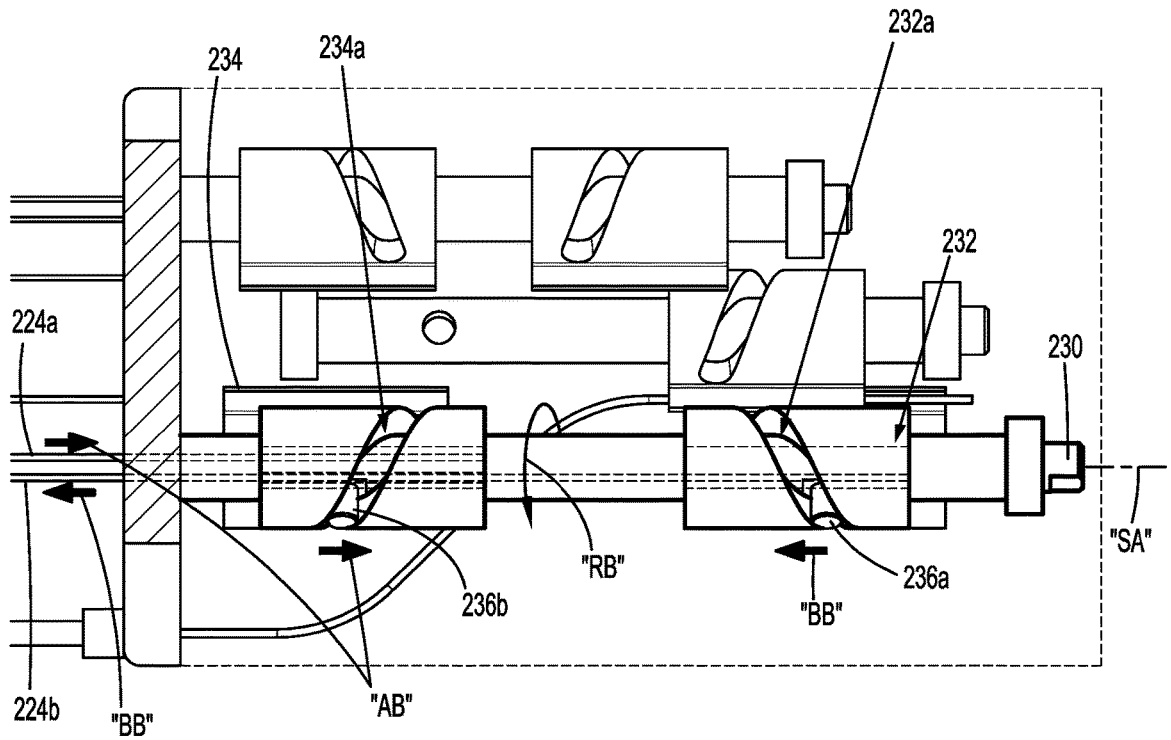

With reference to FIGS. 20 and 21, instrument cassette assembly 202 of surgical instrument 200 includes an outer housing assembly 208 and an inner housing assembly 210 supported within outer housing assembly 208. Inner housing assembly 210 includes an actuator housing 212 and an actuator assembly 214 that is supported within inner housing assembly 210. Actuator housing 212 defines a plurality of actuator cavities 212a defined therein for receiving actuator assembly 214.

Turning now to FIGS. 20-24, actuator assembly 214 of inner housing assembly 210 includes a first set of cable actuator assemblies 216, a second set of cable actuator assemblies 218, and an axial actuator assembly 220 that are secured to a support plate 222. Notably, adjacent cable actuator assemblies 216, 218 may be disposed out of phase and/or offset from one another by, for example, 90 degrees (e.g., orthogonal to one another), and with axial actuator assembly 220 centered between first and second sets of cable actuator assemblies 216, 218 to conserve space and reduce size requirements of inner housing assembly 210. Support plate 222 defines bores 222a for supporting cable and actuator assemblies 216, 218, and 220 therein, and cable passages 222b for receiving cables 224 of cable actuator assembles 216, 218 therethrough. Although the first set of cable actuator assemblies 216 are shown to be longer than second set of cable actuator assemblies 218, and the second set of cable actuator assemblies 218 is otherwise substantially the same as the first set of cable actuator assemblies 218. Indeed, the first and second set of cable actuator assemblies 216, 218 may have any suitable length. Axial actuator assembly 220 is coupled to a drive cable 226 that extends through a tube 228 extending from support plate 222 that couples to elongated shaft assembly 204.

Each cable actuator assembly 216, 218 of actuator assembly 214 includes a spindle 230, an upper crank 232, a lower crank 234, an upper pin 236a, a lower pin 236b, an upper bearing 238a, and a lower bearing 238b.

Spindles 230 of actuator assemblies 216, 218 include an upper peg 230a extending from a first end thereof and a lower peg 230b extending from a second end thereof. Upper and lower pegs 230a, 230b secure to upper and lower bearings 238a, 238b, respectively. Upper peg 230a is engageable with movable drive unit 18 to enable movable drive unit 18 to impart rotational drive force on spindles 230 (e.g., through drive couplers—not shown—of drive unit 18). Each spindle 230 further defines an upper pin passage 230c and a lower pin passage 230d that extend transversely through spindle 230 at longitudinally spaced-apart locations and are positioned to receive upper and lower pins 236a, 236b, respectively, in a transverse (e.g., an orthogonal) relationship with spindle 230.

Lower crank 234 of each cable actuator assembly 216, 218 defines a spindle passage 234a longitudinally and centrally therethrough for receiving spindle 230 therethrough. Lower crank 234 further defines a spiral channel 234b in an outer surface thereof. Spiral channel 234b slidably receives lower pin 236b of spindle 230 to enable lower crank 234 to axially slide along a lower portion of spindle 230, as indicated by arrows "AA" (e.g., distally) and "AB" (e.g., proximally) when spindle 230 rotates about spindle axis "SA" relative to lower crank 234, as indicated by arrows "RA" (e.g., clockwise) and "RB" (e.g., counterclockwise) shown in FIGS. 26 and 27. Lower crank 234 further includes a spine 234c that extends longitudinally along the outer surface of lower crank 234. Spine 234c defines cable channels 234d, 234e longitudinally therethrough that support cables 224. A first cable 224a of cables 224 is secured to lower crank 234 (e.g., via cable channel 234e) and translates in the same direction and simultaneously with lower crank 234 (e.g., as indicated by arrows "AA" and "AB"). A second cable 224b of cables 224 is slidably movable through cable channel 234d of lower crank 234 and relative to lower yoke 234 as upper crank 232 translates relative to spindle 230. Second cable 224b is secured to upper crank 232 and movable with upper crank 232.

Upper crank 232 of each cable actuator assembly 216, 218 is substantially like lower crank 234 but includes a spiral channel 232a that turns along the outer surface thereof in an opposite direction as compared to spiral channel 234b of lower crank 234. And spiral channel 232a of upper crank 232 slidably receives upper pin 236a of spindle 230 to axially slide upper crank 232 along an upper portion of spindle 230, as indicated by arrows "BA" (e.g., proximally) and "BB" (e.g., distally), when spindle 230 rotates about spindle axis "SA" and relative to upper crank 232, as indicated by arrows "RA" (e.g., clockwise) and "RB" (e.g., counterclockwise) shown in FIGS. 26 and 27. Upper and lower cranks 234, 236 are positioned to translate in opposite axial directions relative to one another along spindle axis "SA" as upper and lower cranks 234, 236 rotate about spindle 230 and spindle axis "SA." Notably, upper crank 232 further includes a spine 232x that supports and is secured to second cable 224b to enable second cable 224b to translate with upper crank 232 and relative to lower crank 234, as indicated by arrows "BA" and "BB." Upper crank 232 is separate and disconnected from first cable 224a.

Axial actuator assembly 220 is substantially like cable actuator assemblies 216, 218, but includes a spindle 230, an upper crank 232, an upper pin 236a, an upper bearing 238a, and a lower bearing 238b (e.g., there is no lower crank or lower pin). Upper crank 232 is coupled to drive cable 226 and axially translatable upon rotation of spindle 230 thereof to translate drive cable 226 and impart axial drive force through drive cable 226 to, for example, end effector 106.

Turning now to FIGS. 28-42, surgical instrument system 70 of robotic surgical system 10 includes insertion tube 16 and a plurality of surgical instruments 300 that is insertable through insertion tube 16. Although only three surgical instruments 300 are shown, surgical instrument system 70 can include any number and/or type of surgical instruments such as graspers 26 and endoscope 28 as noted above.

Figure 30:
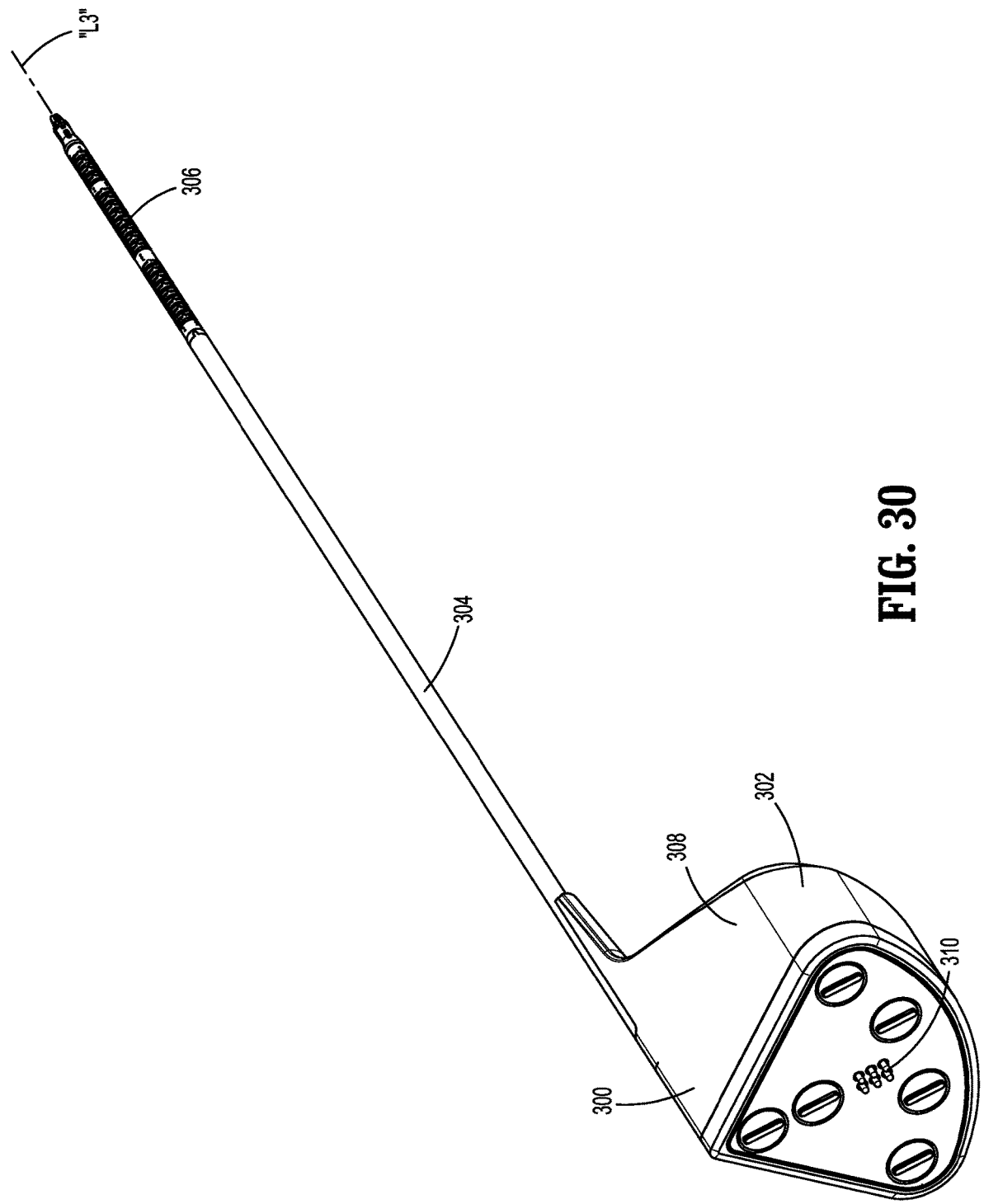
FIG. 30 is a perspective view of one of the surgical instruments of FIG. 28.
Figure 31:
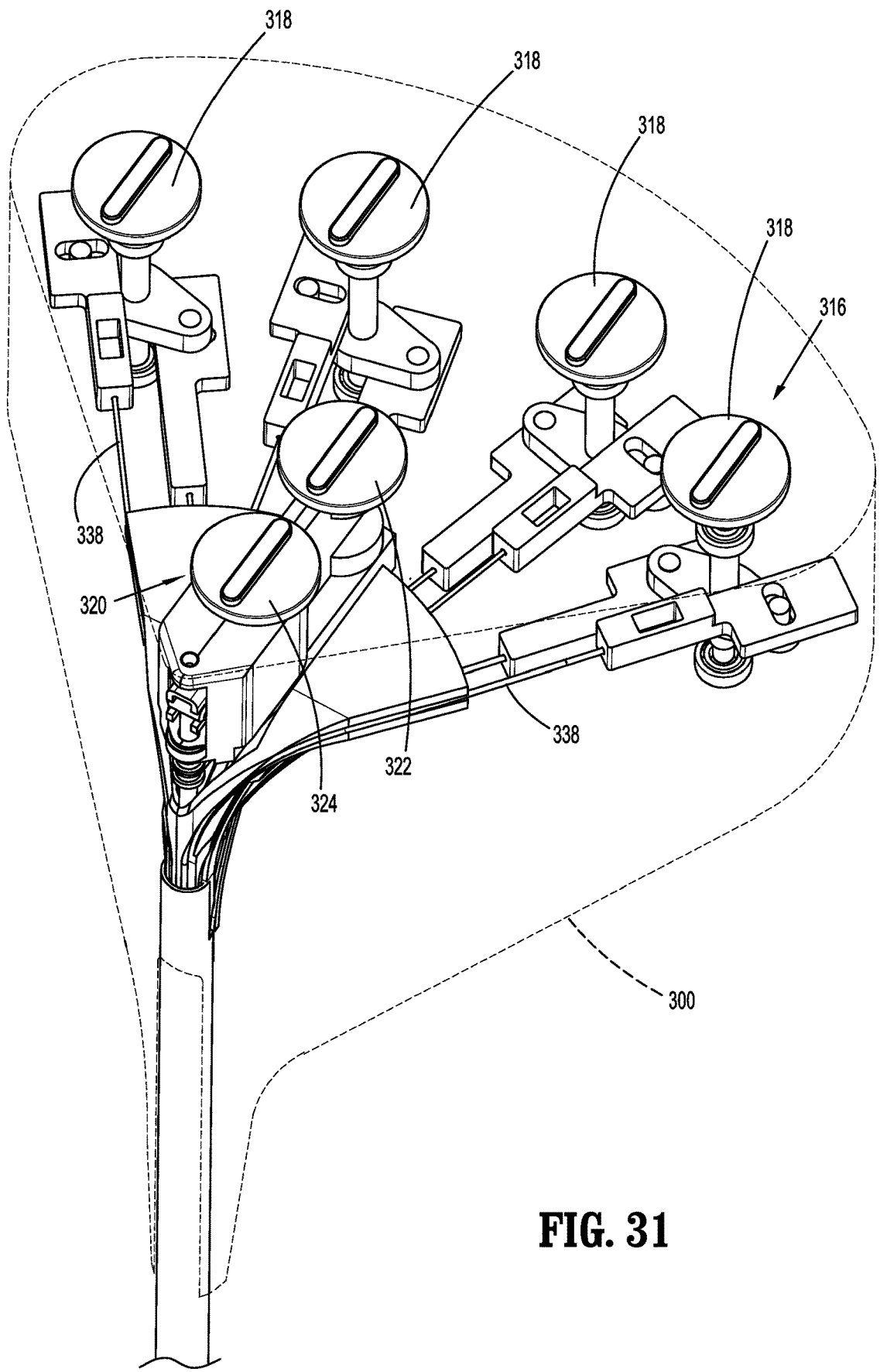
FIG. 31 is an enlarged, perspective view of an instrument cassette assembly of the surgical instrument of FIG. 30.

As seen in FIG. 30, surgical instrument 300 of surgical instrument system 70 defines a longitudinal axis "L3" and includes an instrument cassette assembly 302 on a proximal end portion thereof and an elongated shaft assembly 304 that extends from instrument cassette assembly 302 to an end effector 306 (FIG. 7) supported on a distal end portion of elongated shaft assembly 304. End effector 306 is actuatable by instrument cassette assembly 302 for effectuating a surgical procedure. Indeed, actuating end effector 306 can cause end effector 306 to, for example, articulate, pivot, clamp, rotate, etc. relative to the longitudinal axis "L3" of surgical instrument 300 for repositioning end effector 306 and/or for treating tissue "T" of the patient "P" as noted above with respect to end effector 106 (see FIGS. 2-4).

Figure 28:
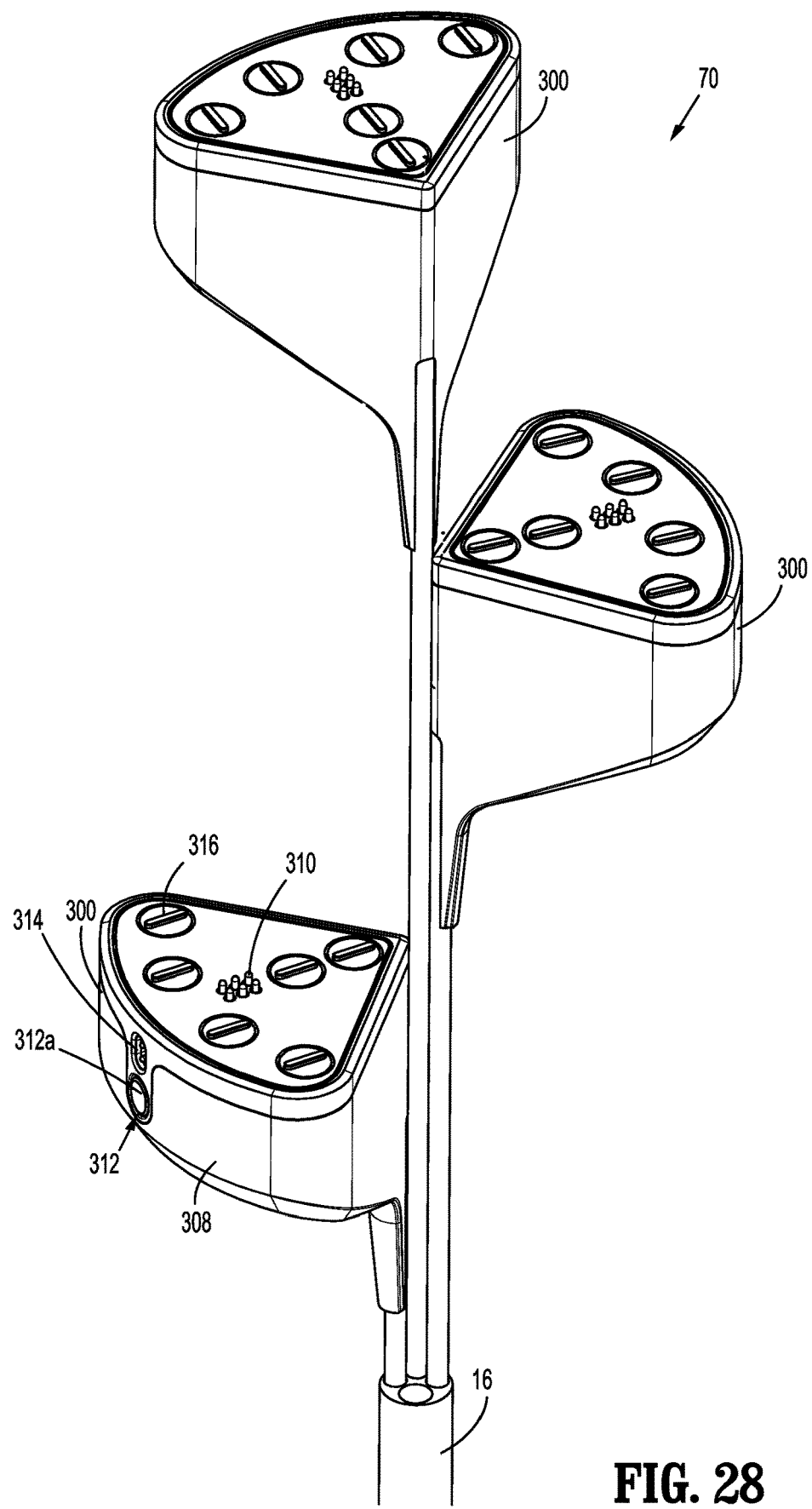
FIG. 28 is an enlarged, perspective view of proximal portions of surgical instruments of yet another surgical instrument system of the robotic surgical system of FIG. 1.
Figure 29:
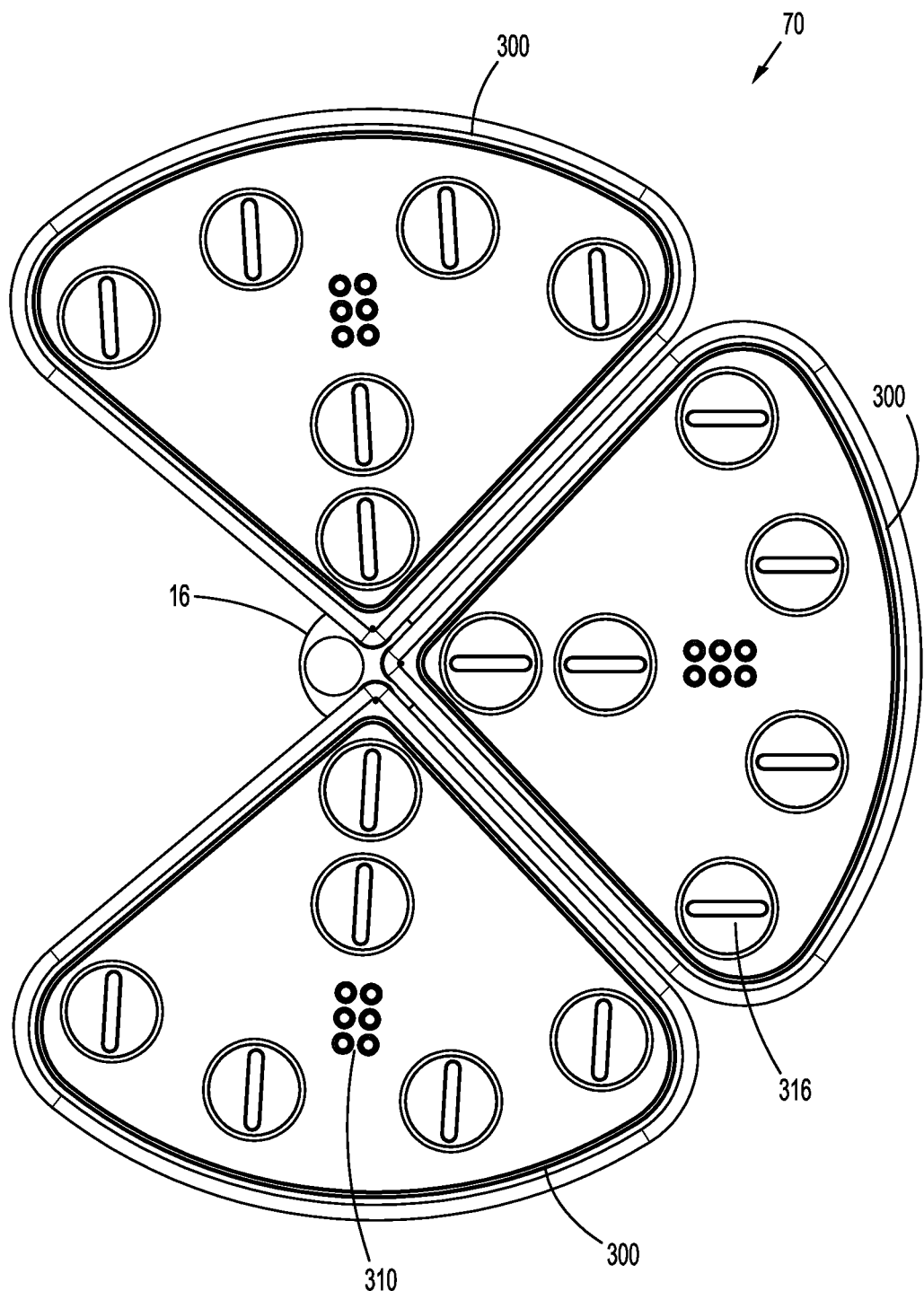
FIG. 29 is an enlarged, top view of FIG. 28.

With reference to FIGS. 28-30, instrument cassette assembly 302 of surgical instrument 300 includes an outer housing assembly 308 that supports an ID board 310, a latch release mechanism 312 having a button release 312a for selectively removing surgical instrument from movable drive unit 18, and an electrosurgical socket 314 for selectively connecting to an electrosurgical energy source via an electrosurgical cable (not shown). Instrument cassette assembly 302 further includes an actuator system 316 supported within outer housing assembly 308 for actuating end effector 306.

Turning now to FIGS. 31-36, actuator system 316 includes a plurality of cable actuator assemblies 318 and a drive actuator assembly 320. The drive actuator assembly 320 includes an axial actuator assembly 322 and a rotation actuator assembly 324.

Figure 32:
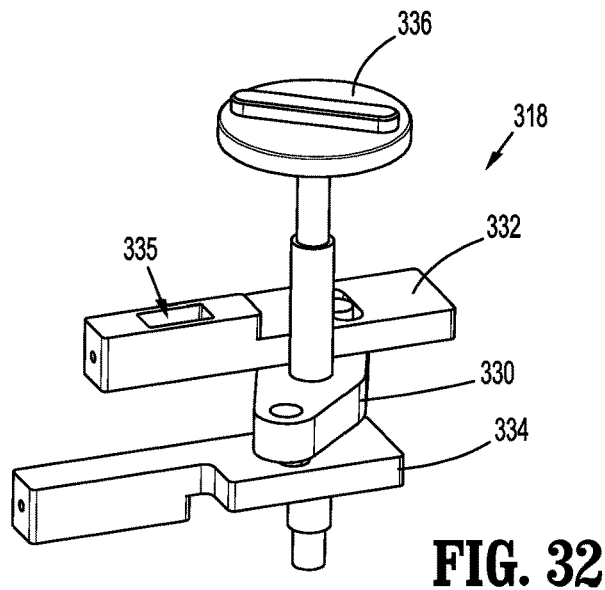
FIG. 32 is an enlarged, perspective view of a cable actuator assembly of the instrument cassette assembly of FIG. 31.
Figure 33:
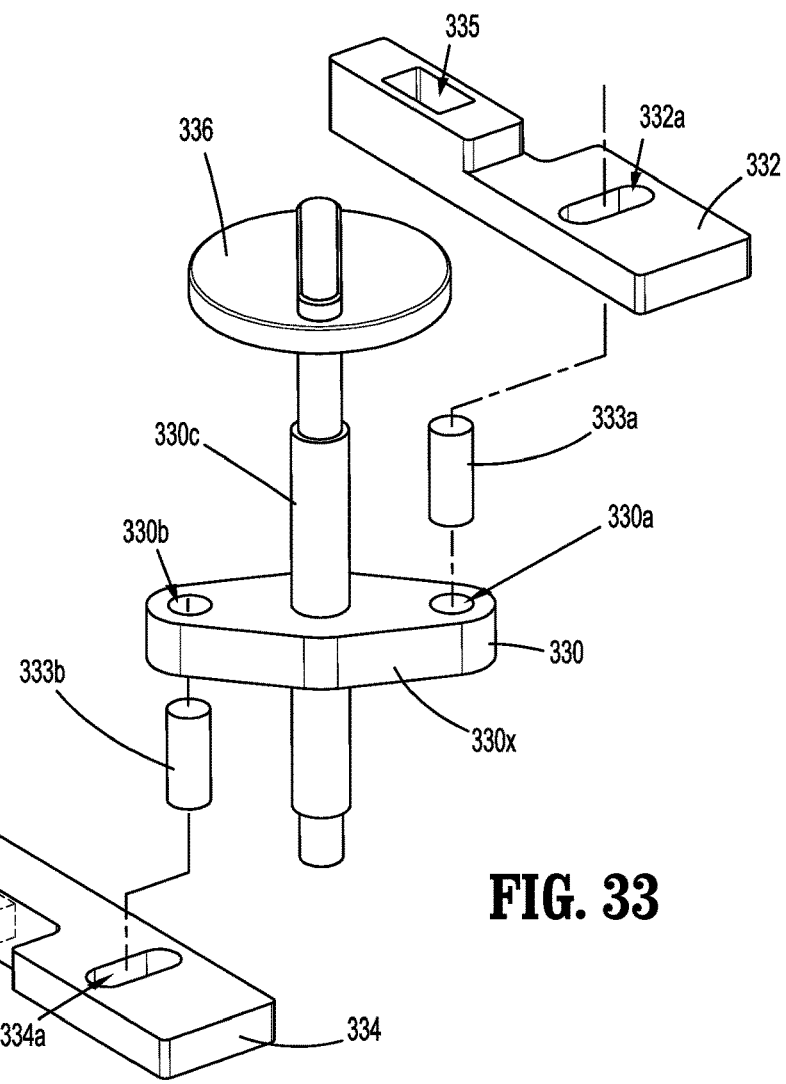
FIG. 33 is an enlarged, perspective view, with parts separated, of the cable actuator assembly of FIG. 32.

With reference to FIG. 32, each cable actuator assembly 318 of the actuator system 316 includes a crank 330, an upper slider 332, a lower slider 334, and a driver 336. The upper slider 332 secured to an upper surface of crank body 330x, via a first pin 333a, on a first side of crank body 330x, the lower slider 334 secured to a lower surface of crank body 330x, via a second pin 333b, on a second side of crank body 330x. Crank body 330x defines a first opening 330a on the first side of crank body 330x that receives a lower portion of the first pin 333a and a second opening 330b on the second side of crank body 330x that receives an upper portion of the second pin 333b. Upper slider 332 defines an elongated pin slot 332a that receives an upper portion of the first pin 333a and lower slider 334 defines an elongated pin slot 334a that receives a lower portion of the second pin 333b. Upper and lower sliders 332, 334 further define ferrule openings 335 that support ferrules (not shown) therein for securing cables 338 of cable actuator assembly 318 to respective upper and lower sliders 332, 334. Crank 330 further includes a drive shaft 330c that extends from the upper and lower surfaces of crank body 330x and nonrotatably supports driver 336 so that rotation of driver 336 imparts rotational force to crank 330.

In some aspects, each cable actuator assembly 318 may be provided in the form of a rack and pinion arrangement. For example, crank 330 may be a pinion, and upper slider 332 and lower slider 334 are in the form of racks so that teeth of these respect rack and pinion feature engage one another. Indeed, upper and lower sliders 332, 334 may be disposed in the same plane as one another (e.g., vertically aligned or in registration), and/or vertically offset from one another such that one is higher and/or lower than the other along a vertical or central axis (not explicitly shown) extending through a center of crank 330.

Figure 34:
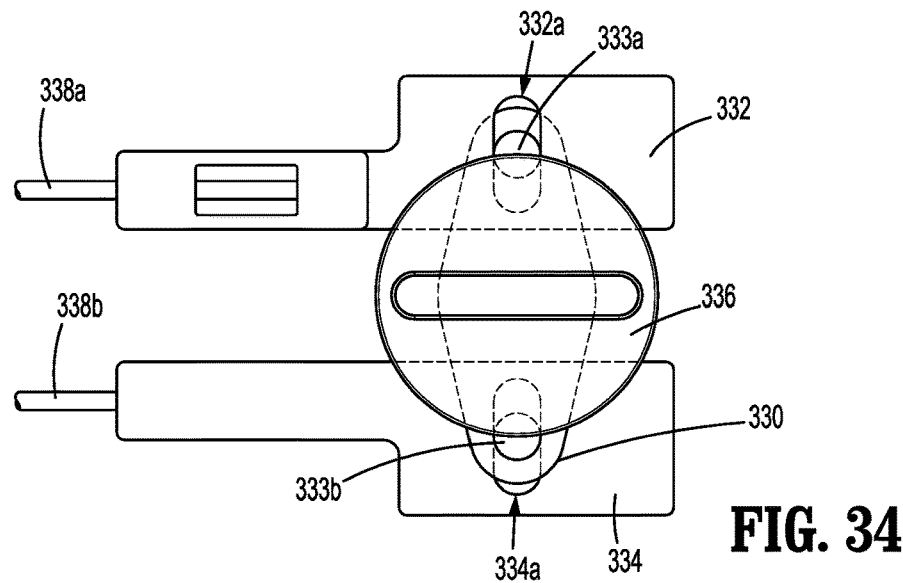
FIGS. 34-36 are progressive views of the cable actuator assembly of FIG. 32 being actuated.
Figure 35:
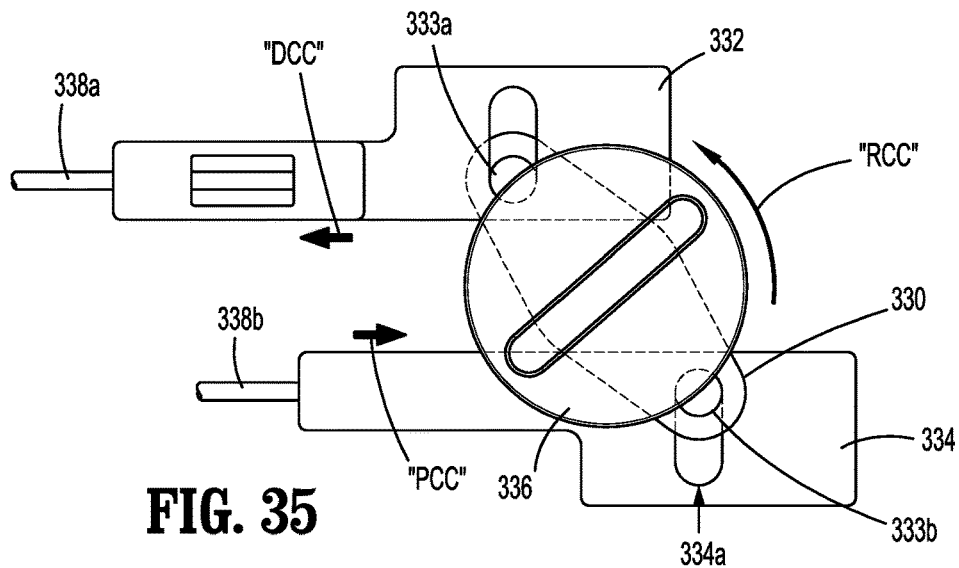
Figure 36:
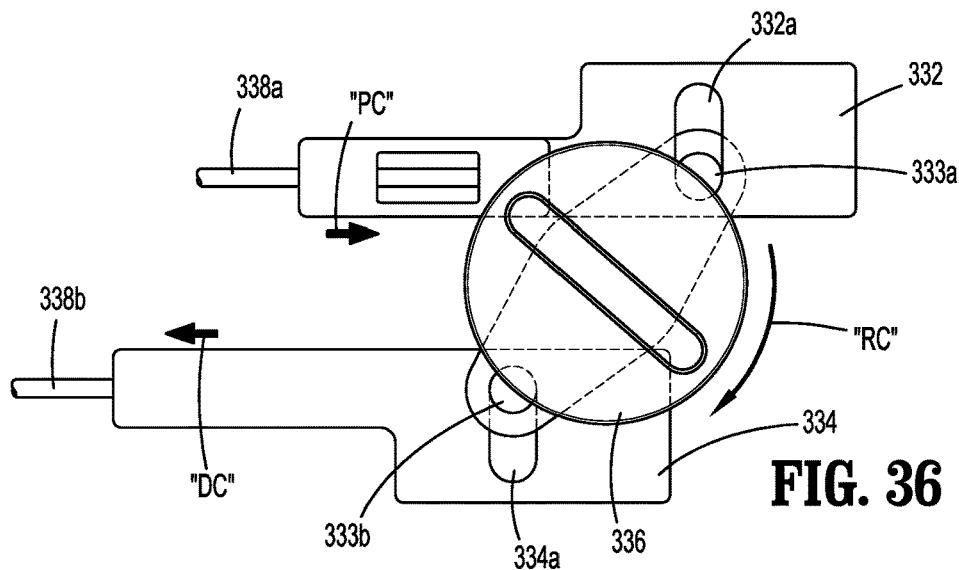
Figure 38:
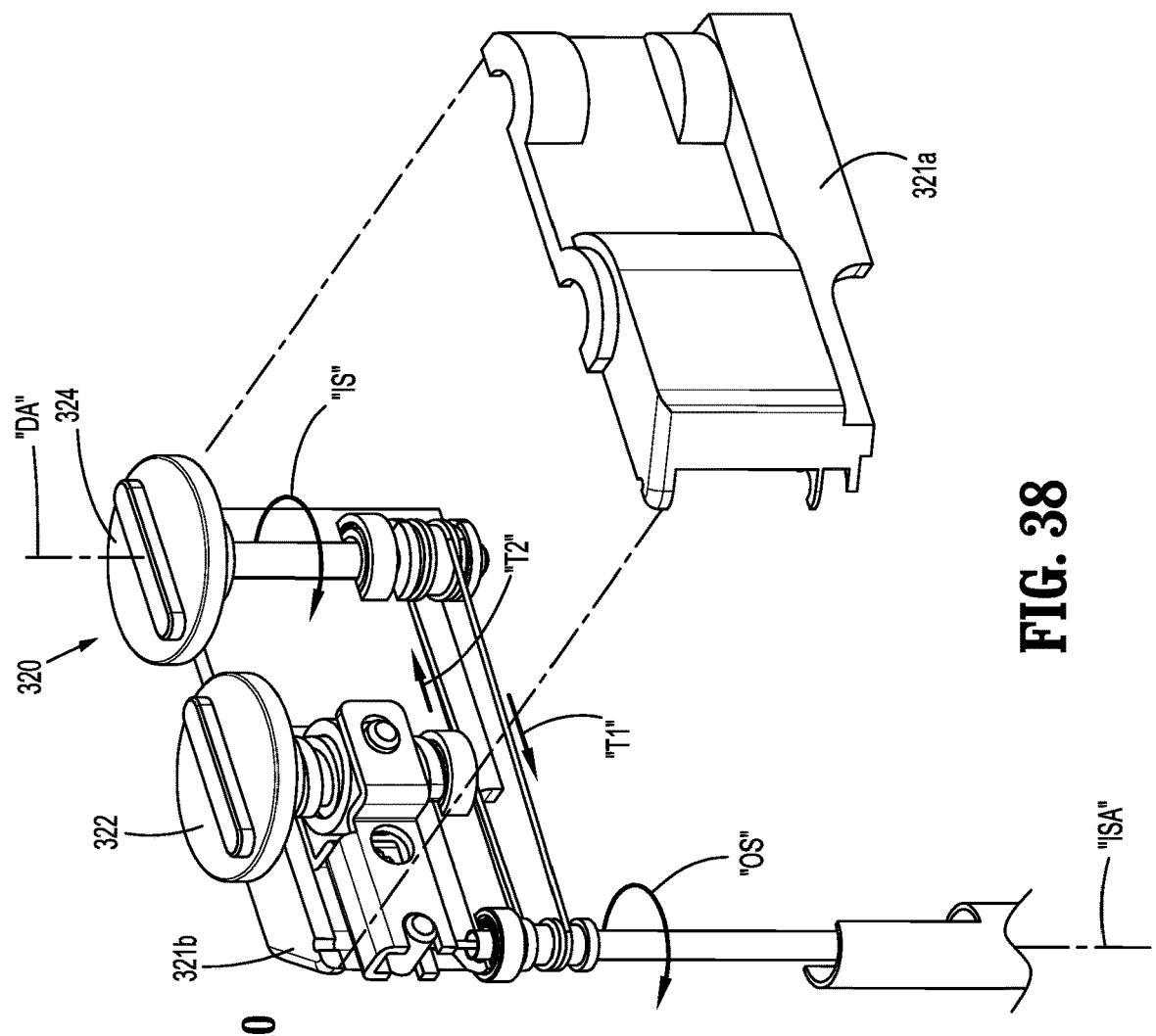
FIG. 38 is an enlarged perspective view, with parts separated, of a drive actuator assembly of the instrument cassette assembly of FIG. 31, the drive actuator assembly including an axial actuator assembly and a rotation actuator assembly, the rotation actuator assembly shown being actuated.
Figure 37:
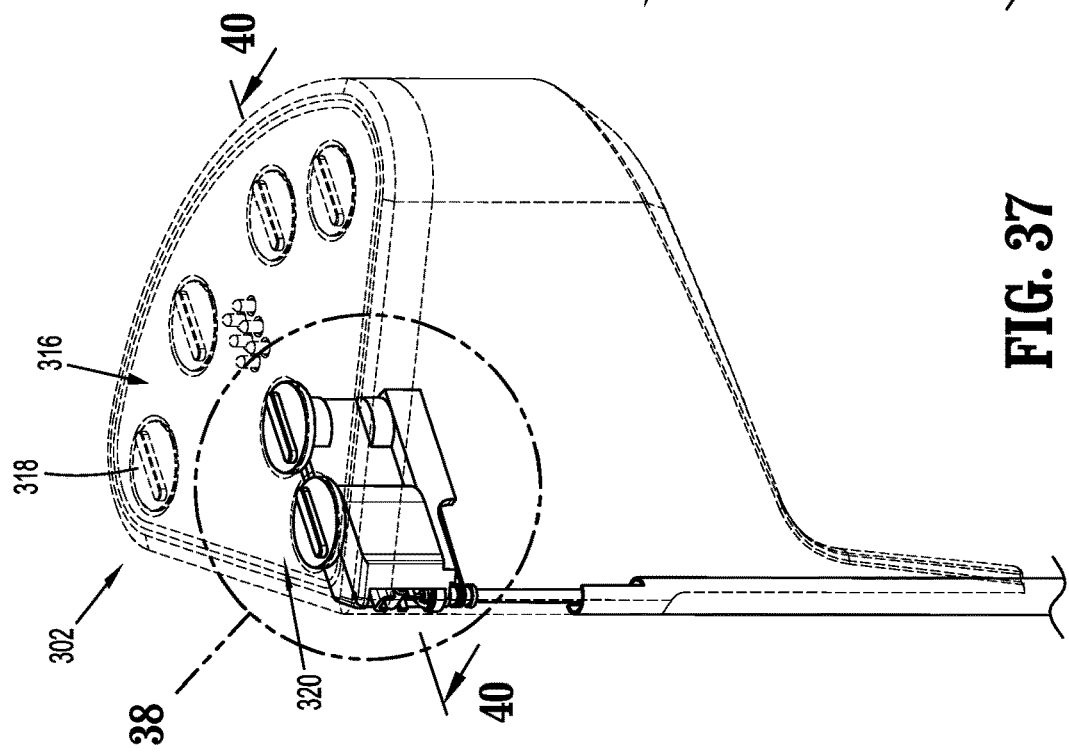
FIG. 37 is a perspective view of the instrument cassette assembly of FIG. 31 with portions thereof shown in phantom for clarity.
Figure 39:
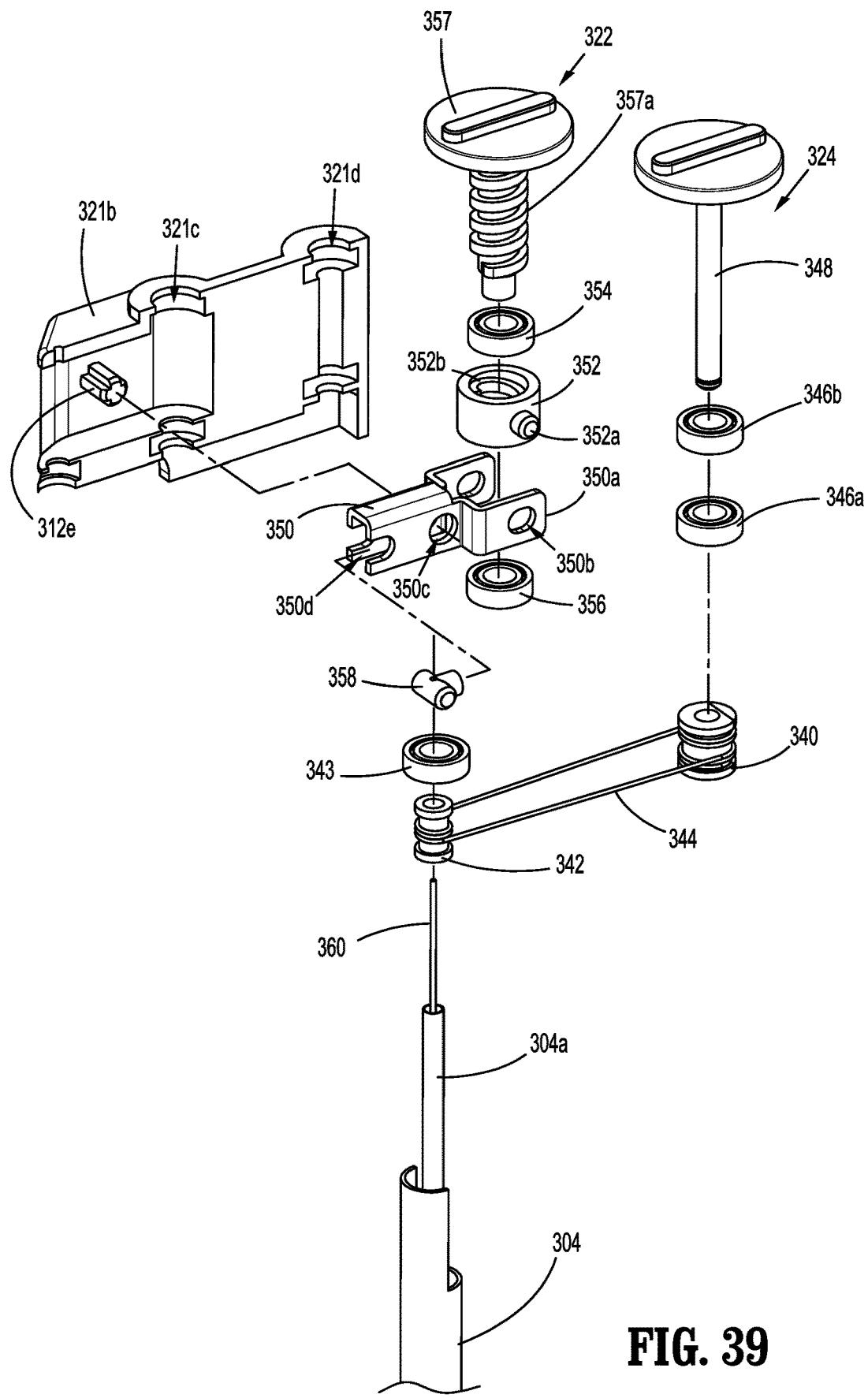
FIG. 39 is a perspective view, with parts separated, of the drive actuator assembly of FIG. 38.
Figure 40:
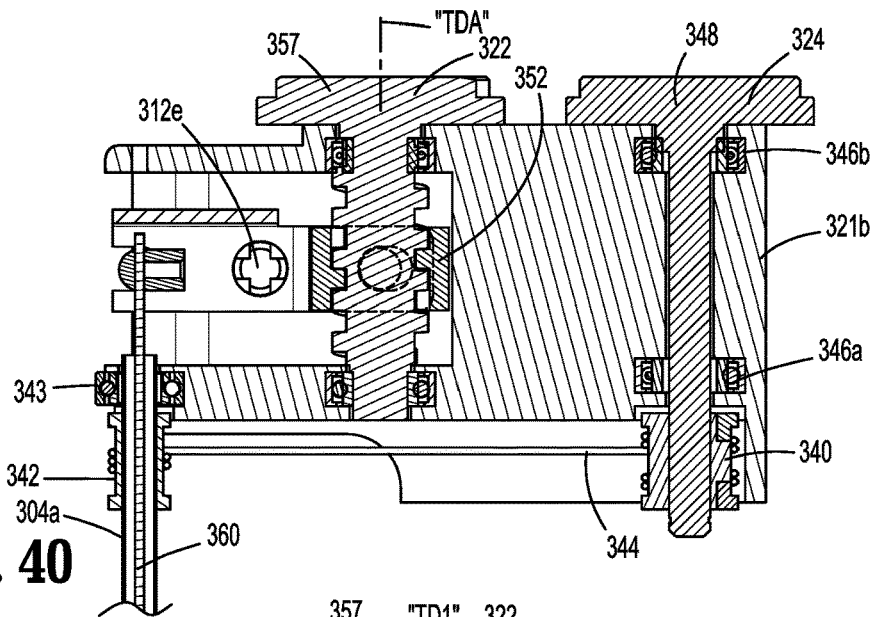
FIGS. 40-42 are progressive, cross-sectional views as taken along section line 40-40 shown in FIG. 37 and illustrating an actuation of the axial actuator assembly of the drive actuator assembly of FIG. 38.

As seen in FIGS. 34-36, rotation of driver 336 in a first direction (e.g., counterclockwise), as indicated by arrow "RCC," rotates crank 330 such that first pin 333a moves inwardly along elongated pin slot 332a of upper slider 332 to an actuated position and second pin 333b moves inwardly along elongated pin slot 334a of lower slider 334 to an actuated position. As crank 330 is rotated in the first direction, crank 330 and first pin 333a cause upper slider 332 to translate distally as indicated by arrow "DCC" while crank 330 and second pin 333b cause lower slider 334 to translate proximally as indicated by arrow "PCC." Rotation of driver 336 in a second direction opposite to the first direction (e.g., clockwise), as indicated by arrow "RC," causes crank 330 to rotate such that first and second ins 33a, 33b move to the actuated position within respective elongated pin slots 332a, 334a of upper and lower sliders 332, 334 and drive upper slider 332 in a proximal direction, as indicated by arrow "PC," and lower slider 334 in a distal direction, as indicated by arrow "DC." As upper and lower sliders 332, 334 translate between proximal and distal positions, cables 338 secured thereto translate with the respective upper and lower sliders 332, 334. For instance, when upper slider 332 translates distally (or proximally), a first cable 338a of cables 338 secured to upper slider 332 translates distally (or proximally) with upper slider 332, and vice versa. Similarly, when lower slider 334 translates proximally (or distally), a second cable 338b of cables 338 secured to lower slider 334 translates proximally (or distally) with lower slider 334, and vice versa.

With reference to FIGS. 37-42, drive actuator assembly 320 of actuator system 316 includes an actuator housing 321 having a first housing portion 321a and a second housing portion 321b that define actuator mounts 321c, 321d for supporting the axial actuator assembly 322 and the rotation actuator assembly 324 between the first and second housing portions 321a, 321b. Second housing portion 312b further includes a mounting protrusion 312e extending from a sidewall thereof.

Rotation actuator assembly 324 of drive actuator assembly 320 includes an input spool 340, an output spool 342, a rotation cable 344 that couples to (e.g., wraps around) input and output spools 340, 342, bearings 346a, 346b, and a driver 348 that nonrotatably couples to input spool 340. Cable 344 may have any number of windings about input and output spools 340, 342 to enable rotational force to be transferred between input and output spools 340, 342. Notably, elongated shaft assembly 304 of surgical instrument 300 includes an inner shaft 304a to which output spool 342 nonrotatably couples, and which is coupled to actuator housing 321 by a shaft bearing 343. Output spool 342 imparts rotational force to inner shaft 304a from input spool 340 as rotation cable 344 rotates output spool 342 about inner shaft axis "ISA," as indicated by arrow "OS," (as rotation cable 344 translates-see arrows "T1" and "T2") in response to rotation of driver 348 about driver axis "DA," as indicated by arrow "IS."

Axial actuator assembly 322 of drive actuator assembly 320 includes a clevis 350, a threaded nut 352 mounted to clevis 350 via pins 352a thereof, an upper bearing 354, a lower bearing 356, a threaded driver 357 having threads 357a, and a cable pivot 358. Threads 357a of threaded driver 357 are threadedly engageable with threads 352b of threaded nut 352 to enable threaded nut 352 to translate along threaded driver 357, as indicated by arrows "N1" and "N2," when threaded driver 357 is rotated, as indicated by arrows "TD1" and "TD2" (e.g., clockwise and/or counterclockwise about axis "TDA." Clevis 350 defines a nut mount 350a on a first end thereof that defines pin holes 350b therethrough for receiving pins 352a of threaded nut 352 therein. Clevis 350 further defines a protuberance hole 350c that receives mounting protrusion 312e of second housing portion 312b for securing clevis 350 to actuator housing 321. A second end of clevis 350 defines a cable pivot channel 350d for receiving cable pivot 358 and an axial drive cable 360 therein. Axial drive cable 360 is coupled to cable pivot 358 on a first end thereof and extends through inner shaft 304a to enable a second end of axial drive cable 360 to secure to end effector 306 for imparting axial drive force on end effector 306.

Figure 41:
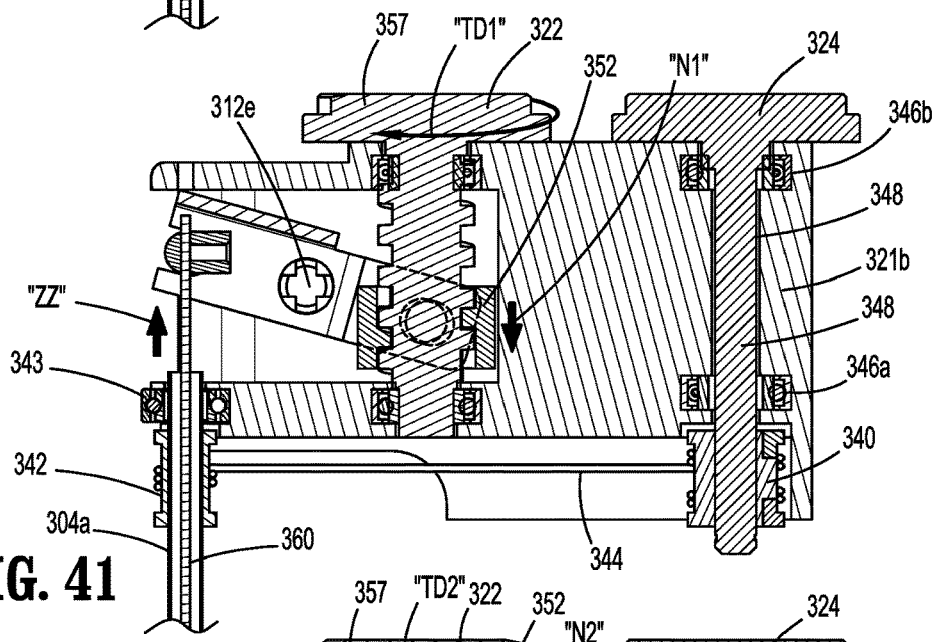
Figure 42:
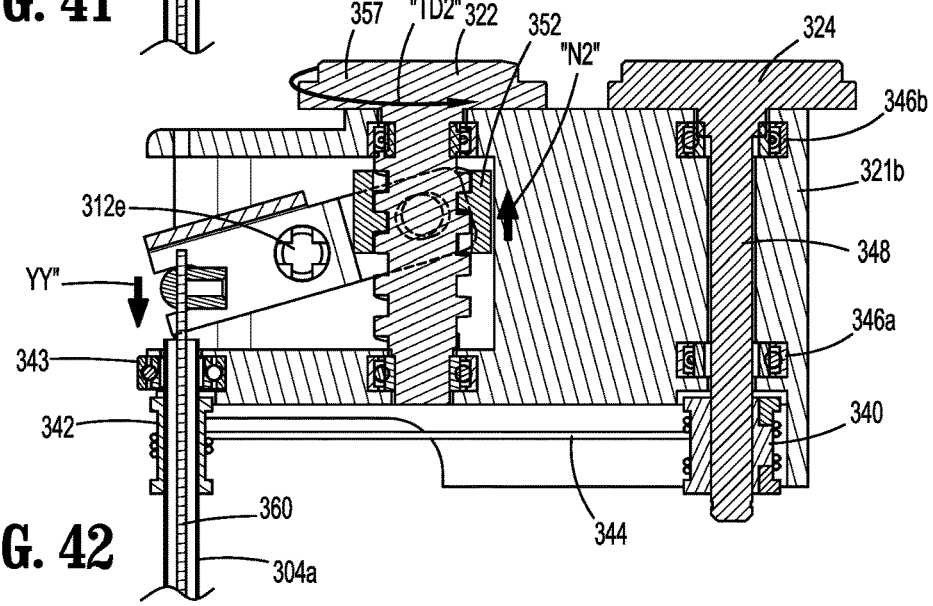

As seen in FIGS. 41 and 42, as threaded nut 352 translates along threaded driver 357, the first end of clevis 350 pivots about pins 352a and mounting protrusion 312e, relative to threaded nut 352, such that the second end of clevis 350 moves axial drive cable 360 between an extended position (FIG. 42) and a retracted position (FIG. 41), as indicated by arrows "ZZ" and "YY." The second end of clevis 350 also pivot relative to cable pivot 350 as axial drive cable 360 is moved between the extended and retracted positions to impart axial force to end effector 306.

The disclosed structure can include any suitable mechanical, electrical, and/or chemical components for operating the disclosed system or components thereof. For instance, such electrical components can include, for example, any suitable electrical and/or electromechanical, and/or electrochemical circuitry, which may include or be coupled to one or more printed circuit boards. As appreciated, the disclosed computing devices (and/or servers) can include, for example, a "controller," "processor," "digital processing device" and like terms, and which are used to indicate a microprocessor or central processing unit (CPU). The CPU is the electronic circuitry within a computer that carries out the instructions of a computer program by performing the basic arithmetic, logical, control and input/output (I/O) operations specified by the instructions, and by way of non-limiting examples, include server computers. In some aspects, the controller includes an operating system configured to perform executable instructions. The operating system is, for example, software, including programs and data, which manages hardware of the disclosed apparatus and provides services for execution of applications for use with the disclosed apparatus. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. In some aspects, the operating system is provided by cloud computing.

In some aspects, the term "controller" may be used to indicate a device that controls the transfer of data from a computer or computing device to a peripheral or separate device and vice versa, and/or a mechanical and/or electro-mechanical device (e.g., a lever, knob, etc.) that mechanically operates and/or actuates a peripheral or separate device.

In aspects, the controller includes a storage and/or memory device. The storage and/or memory device is one or more physical apparatus used to store data or programs on a temporary or permanent basis. In some aspects, the controller includes volatile memory and requires power to maintain stored information. In various aspects, the controller includes non-volatile memory and retains stored information when it is not powered. In some aspects, the non-volatile memory includes flash memory. In certain aspects, the non-volatile memory includes dynamic random-access memory (DRAM). In some aspects, the non-volatile memory includes ferroelectric random-access memory (FRAM). In various aspects, the non-volatile memory includes phase-change random access memory (PRAM). In certain aspects, the controller is a storage device including, by way of non-limiting examples, CD-ROMs, DVDs, flash memory devices, magnetic disk drives, magnetic tapes drives, optical disk drives, and cloud-computing-based storage. In various aspects, the storage and/or memory device is a combination of devices such as those disclosed herein.

In various aspects, the memory can be random access memory, read-only memory, magnetic disk memory, solid state memory, optical disc memory, and/or another type of memory. In various aspects, the memory can be separate from the controller and can communicate with the processor through communication buses of a circuit board and/or through communication cables such as serial ATA cables or other types of cables. The memory includes computer-readable instructions that are executable by the processor to operate the controller. In various aspects, the controller may include a wireless network interface to communicate with other computers or a server. In aspects, a storage device may be used for storing data. In various aspects, the processor may be, for example, without limitation, a digital signal processor, a microprocessor, an ASIC, a graphics processing unit ("GPU"), field-programmable gate array ("FPGA"), or a central processing unit ("CPU").

The memory stores suitable instructions and/or applications, to be executed by the processor, for receiving the sensed data (e.g., sensed data from camera), accessing storage device of the controller, generating a raw image based on the sensed data, comparing the raw image to a calibration data set, identifying an object based on the raw image compared to the calibration data set, transmitting object data to a post-processing unit, and displaying the object data to a graphic user interface. Although illustrated as part of the disclosed structure, it is also contemplated that a controller may be remote from the disclosed structure (e.g., on a remote server), and accessible by the disclosed structure via a wired or wireless connection. In aspects where the controller is remote, it is contemplated that the controller may be accessible by, and connected to, multiple structures and/or components of the disclosed system.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on the disclosed controllers or on a user device, including for example, on a mobile device, an IOT device, or a server system.

In some aspects, the controller includes a display to send visual information to a user. In various aspects, the display is a cathode ray tube (CRT). In various aspects, the display is a liquid crystal display (LCD). In certain aspects, the display is a thin film transistor liquid crystal display (TFT-LCD). In aspects, the display is an organic light emitting diode (OLED) display. In certain aspects, on OLED display is a passive-matrix OLED (PMOLED) or active-matrix OLED (AMOLED) display. In aspects, the display is a plasma display. In certain aspects, the display is a video projector. In various aspects, the display is interactive (e.g., having a touch screen) that can detect user interactions/gestures/responses and the like. In some aspects, the display is a combination of devices such as those disclosed herein.

The controller may include or be coupled to a server and/or a network. As used herein, the term "server" includes "computer server," "central server," "main server," and like terms to indicate a computer or device on a network that manages the disclosed apparatus, components thereof, and/or or resources thereof. As used herein, the term "network" can include any network technology including, for instance, a cellular data network, a wired network, a fiber-optic network, a satellite network, and/or an IEEE 802.11a/b/g/n/ac wireless network, among others.

In various aspects, the controller can be coupled to a mesh network. As used herein, a "mesh network" is a network topology in which each node relays data for the network. All mesh nodes cooperate in the distribution of data in the network. It can be applied to both wired and wireless networks. Wireless mesh networks can be considered a type of "Wireless ad hoc" network. Thus, wireless mesh networks are closely related to Mobile ad hoc networks (MANETs). Although MANETs are not restricted to a specific mesh network topology, Wireless ad hoc networks or MANETs can take any form of network topology. Mesh networks can relay messages using either a flooding technique or a routing technique. With routing, the message is propagated along a path by hopping from node to node until it reaches its destination. To ensure that all its paths are available, the network must allow for continuous connections and must reconfigure itself around broken paths, using self-healing algorithms such as Shortest Path Bridging. Self-healing allows a routing-based network to operate when a node breaks down or when a connection becomes unreliable. As a result, the network is typically quite reliable, as there is often more than one path between a source and a destination in the network. This concept can also apply to wired networks and to software interaction. A mesh network whose nodes are all connected to each other is a fully connected network.

In some aspects, the controller may include one or more modules. As used herein, the term "module" and like terms are used to indicate a self-contained hardware component of the central server, which in turn includes software modules. In software, a module is a part of a program. Programs are composed of one or more independently developed modules that are not combined until the program is linked. A single module can contain one or several routines, or sections of programs that perform a particular task.

As used herein, the controller includes software modules for managing various aspects and functions of the disclosed system or components thereof.

The disclosed structure may also utilize one or more controllers to receive various information and transform the received information to generate an output. The controller may include any type of computing device, computational circuit, or any type of processor or processing circuit capable of executing a series of instructions that are stored in memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, cause the one or more processors to perform one or more methods and/or algorithms.

The phrases "in an aspect," "in aspects," "in various aspects," "in some aspects," or "in other aspects" may each refer to one or more of the same or different aspects in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques).

Certain aspects of the present disclosure may include some, all, or none of the above advantages and/or one or more other advantages readily apparent to those skilled in the art from the drawings, descriptions, and claims included herein. Moreover, while specific advantages have been enumerated above, the various aspects of the present disclosure may include all, some, or none of the enumerated advantages and/or other advantages not specifically enumerated above.

The aspects disclosed herein are examples of the disclosure and may be embodied in various forms. For instance, although certain aspects herein are described as separate, each of the aspects herein may be combined with one or more of the other aspects herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

Any of the herein described methods, programs, algorithms, or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to all such states. Reference to a program may encompass the actual instructions and/or the intent of those instructions.

Securement of any of the components of the disclosed devices may be effectuated using known securement techniques such welding, crimping, gluing, fastening, etc.

Persons skilled in the art will understand that the structures and methods specifically described herein and shown in the accompanying figures are non-limiting exemplary aspects, and that the description, disclosure, and figures should be construed merely as exemplary of aspects. It is to be understood, therefore, that this disclosure is not limited to the precise aspects described, and that various other changes and modifications may be effectuated by one skilled in the art without departing from the scope or spirit of the disclosure. Additionally, the elements and features shown or described in connection with certain aspects may be combined with the elements and features of certain other aspects without departing from the scope of this disclosure, and that such modifications and variations are also included within the scope of this disclosure. Accordingly, the subject matter of this disclosure is not limited by what has been particularly shown and described.

What is claimed is:

1. A robotic surgical system, comprising:
a drive unit;
a surgical instrument removably connected to the drive unit, the surgical instrument including:
an elongated shaft assembly having a proximal end portion and a distal end portion;
an end effector supported on the distal end portion of the elongated shaft assembly; and
an instrument cassette assembly supported on the proximal end portion of the elongated shaft assembly, the instrument cassette assembly including:
a cassette housing; and
an actuator system supported in the cassette housing and operably coupled to the end effector for operating the end effector, the actuator system including:
a cable actuator assembly including a plurality of cables that extends from the cassette housing to the end effector for manipulating the end effector;
an actuator shaft assembly supported in the elongated shaft assembly and defining a longitudinal axis, the actuator shaft assembly including a first inner shaft, and a second inner shaft slidably advanceable through the first inner shaft;
a rotation actuator assembly coupled to the first inner shaft of the actuator shaft assembly and positioned to rotate the first inner shaft of the actuator shaft assembly about the longitudinal axis and relative to the elongated shaft assembly for imparting rotational force to the end effector; and
an axial actuator assembly coupled to the second inner shaft of the actuator shaft assembly and positioned to axially translate the second inner shaft of the actuator shaft assembly relative to the longitudinal axis and relative to the elongated shaft assembly for imparting axial force to the end effector.

2. The robotic surgical system of claim 1, wherein the cable actuator assembly includes a crank, a first slider, and a second slider, the first and second sliders coupled to the crank.

3. The robotic surgical system of claim 2, wherein the crank is rotatable to linearly translate the first and second sliders relative to one another.

4. The robotic surgical system of claim 3, wherein the first slider supports a first cable of the plurality of cables and the second slider supports a second cable of the plurality of cables.

5. The robotic surgical system of claim 3, wherein the crank is coupled to a driver that is engaged with the drive unit, the driver configured to impart rotational force on the crank.

6. The robotic surgical system of claim 1, wherein the rotation actuator assembly includes a drive wheel and a belt drive shaft supporting a belt, the belt coupled to the actuator shaft assembly and the drive wheel coupled to the belt drive shaft.

7. The robotic surgical system of claim 6, wherein the drive wheel and the belt drive are disposed transverse to one another, the drive wheel configured to rotate the belt drive shaft.

8. The robotic surgical system of claim 6, wherein rotation of the belt drive shaft rotates the belt to rotate the first inner shaft of the actuator shaft assembly.

9. The robotic surgical system of claim 1, wherein the axial actuator assembly includes a drive disc, a drive arm coupled to the drive disc, and a drive plate coupled to the drive arm and to the shaft assembly.

10. The robotic surgical system of claim 9, wherein the drive arm includes a first pin coupled to the drive disc and a second pin coupled to the drive plate, the drive plate defining a pin slot that receives the second pin, the second pin slidable along the pin slot to axially translate the drive plate and the second inner shaft of the actuator shaft assembly as the drive disc rotates.

11. A surgical system, comprising:
a cassette housing;
an elongated shaft assembly having a proximal end portion supported in the cassette housing, and a distal end portion supporting an end effector; and
an actuator system supported in the cassette housing and the elongated shaft, the actuator system including:
a cable actuator assembly including a plurality of cables;
an actuator shaft assembly supported in the elongated shaft assembly and defining a longitudinal axis, the actuator shaft assembly including a first inner shat, and a second inner shaft slidably advanceable through the first inner shaft;
a rotation actuator assembly coupled to the first inner shaft of the actuator shaft assembly and positioned to rotate the first inner shaft of the actuator shaft assembly about the longitudinal axis and relative to the elongated shaft assembly; and
an axial actuator assembly coupled to the second inner shaft of the actuator shaft assembly and positioned to axially translate the second inner shaft of the actuator shaft assembly relative to the longitudinal axis and relative to the elongated shaft assembly.

12. The surgical system of claim 11, wherein the cable actuator assembly includes a crank, a first slider, and a second slider, the first and second sliders coupled to the crank.

13. The surgical system of claim 12, wherein the crank is rotatable to linearly translate the first and second sliders relative to one another.

14. The surgical system of claim 13, wherein the first slider supports a first cable of the plurality of cables and the second slider supports a second cable of the plurality of cables.

15. The surgical system of claim 13, wherein the crank is coupled to a driver, the driver configured to impart rotational force on the crank.

16. The surgical system of claim 11, wherein the rotation actuator assembly includes a drive wheel and a belt drive shaft supporting a belt, the belt coupled to the actuator shaft assembly and the drive wheel coupled to the belt drive shaft.

17. The surgical system of claim 16, wherein the drive wheel and the belt drive are disposed transverse to one another, the drive wheel configured to rotate the belt drive shaft.

18. The surgical system of claim 16, wherein rotation of the belt drive shaft rotates the belt to rotate the first inner shaft of the actuator shaft assembly.

19. The surgical system of claim 11, wherein the axial actuator assembly includes a drive disc, a drive arm coupled to the drive disc, and a drive plate coupled to the drive arm and to the actuator shaft assembly.

20. A surgical instrument for a robotic surgical system, the surgical instrument comprising:

an elongated shaft assembly having a proximal end portion and a distal end portion;

an end effector supported at the distal end portion of the elongated shaft assembly; and an instrument cassette assembly supported on the proximal end portion of the elongated shaft assembly, the instrument cassette assembly including:

a cassette housing; and an actuator system supported in the cassette housing and operably coupled to the end effector for operating the end effector, the actuator system including:

a cable actuator assembly including a plurality of cables that extends from the cassette housing to the end effector for manipulating the end effector;

an actuator shaft assembly supported in the elongated shaft assembly and defining a longitudinal axis, the actuator shaft assembly including a first inner shat, and a second inner shaft slidably advanceable through the first inner shaft;

a rotation actuator assembly coupled to the first inner shaft of the actuator shaft assembly and positioned to rotate the first inner shaft of the actuator shaft assembly about the longitudinal axis and relative to the elongated shaft assembly for imparting rotational force to the end effector; and an axial actuator assembly coupled to the second inner shaft of the actuator shaft assembly and positioned to axially translate the second inner shaft of the actuator shaft assembly relative to the longitudinal axis and relative to the elongated shaft assembly for imparting axial force to the end effector.

* * * * *